(12) United States Patent  (10) Patent No.: US 7,860,729 B2
Stangel  (45) Date of Patent: Dec. 28, 2010

(54) CLINICAL CARE UTILIZATION MANAGEMENT SYSTEM

(76) Inventor: Peter Stangel, 15 Forest Ridge Rd., Nyack, NY (US) 10960

( * ) Notice: Subject to any disclaimer, the term of this patent is extended or adjusted under 35 U.S.C. 154(b) by 520 days.

(21) Appl. No.: 11/530,374

(22) Filed: Sep. 8, 2006

(65) Prior Publication Data

US 2007/0073559 A1    Mar. 29, 2007

Related U.S. Application Data

(63) Continuation-in-part of application No. 09/772,394, filed on Jan. 30, 2001, now Pat. No. 7,734,480.

(60) Provisional application No. 60/247,246, filed on Nov. 13, 2000, provisional application No. 60/714,968, filed on Sep. 8, 2005.

(51) Int. Cl.
    *G06Q 10/00* (2006.01)
(52) U.S. Cl. .................................. 705/2; 705/3; 706/45
(58) Field of Classification Search .............. 348/207.1; 422/68.1; 434/68.1; 600/300; 700/83; 705/2, 705/3, 4, 67; 706/45; 707/104.1, 3; 713/600; 715/506.741
    See application file for complete search history.

(56) References Cited

U.S. PATENT DOCUMENTS

| | | | |
|---|---|---|---|
| 4,667,292 A | | 5/1987 | Mohlenbrock et al. |
| 4,878,175 A | | 10/1989 | Norden-Paul et al. |
| 5,253,164 A | | 10/1993 | Holloway et al. |
| 5,301,105 A | * | 4/1994 | Cummings, Jr. ............... 705/2 |
| 5,410,704 A | | 4/1995 | Norden-Paul et al. |
| 5,471,382 A | * | 11/1995 | Tallman et al. ............... 600/300 |
| 5,557,514 A | | 9/1996 | Seare et al. |
| 5,574,828 A | * | 11/1996 | Hayward et al. ............... 706/45 |
| 5,664,109 A | * | 9/1997 | Johnson et al. ................ 705/2 |
| 5,764,923 A | * | 6/1998 | Tallman et al. ................. 705/3 |
| 5,772,585 A | * | 6/1998 | Lavin et al. ................. 600/300 |
| 5,774,357 A | * | 6/1998 | Hoffberg et al. ............ 713/600 |
| 5,933,136 A | * | 8/1999 | Brown ........................ 715/741 |
| 5,933,809 A | | 8/1999 | Hunt et al. |
| 5,946,659 A | | 8/1999 | Lancelot et al. |
| 5,950,190 A | * | 9/1999 | Yeager et al. .................. 707/3 |

(Continued)

OTHER PUBLICATIONS

Dialog search history_1.*

(Continued)

*Primary Examiner*—Dilek B Cobanoglu
(74) *Attorney, Agent, or Firm*—Greenberg Traurig LLP

(57) ABSTRACT

A computer implemented system for generating an electronic record of a patient clinical encounter in clinical chart format for submission for review by a health care reviewing organization. The system includes a selection interface module adapted to facilitate the selection of one or more reasons for the patient clinical encounter and/or one or more diagnoses. The system also includes a verification module for determining an authorization level for the diagnosis and/or reason for the encounter by referring to data in identified fields. The verification module determines the authorization level prior to the submission of the clinical record via a web browser on the client side to a server computer. The selection interface module facilitates selection of criteria prompts in a prompt pop-up button list by the display of a clickable navigator text field. The navigator field describes prompts selected to meet criteria for the diagnosis and/or reason for the encounter.

5 Claims, 35 Drawing Sheets

U.S. PATENT DOCUMENTS

| | | | |
|---|---|---|---|
| 5,964,700 A * | 10/1999 | Tallman et al. | 600/300 |
| 5,974,389 A | 10/1999 | Clark et al. | |
| 5,991,728 A | 11/1999 | DeBusk et al. | |
| 6,018,713 A * | 1/2000 | Coli et al. | 705/2 |
| 6,047,259 A * | 4/2000 | Campbell et al. | 705/3 |
| 6,049,794 A * | 4/2000 | Jacobs et al. | 706/45 |
| 6,117,073 A * | 9/2000 | Jones et al. | 600/300 |
| 6,177,940 B1 * | 1/2001 | Bond et al. | 434/262 |
| 6,230,142 B1 * | 5/2001 | Benigno et al. | 705/3 |
| 6,234,964 B1 | 5/2001 | Iliff | |
| 6,308,171 B1 * | 10/2001 | De La Huerga | 707/3 |
| 6,341,265 B1 * | 1/2002 | Provost et al. | 705/4 |
| 6,381,611 B1 * | 4/2002 | Roberge et al. | 707/104.1 |
| 6,484,144 B2 | 11/2002 | Martin et al. | |
| 6,597,392 B1 * | 7/2003 | Jenkins et al. | 348/207.1 |
| 6,602,469 B1 * | 8/2003 | Maus et al. | 422/68.1 |
| 7,092,914 B1 * | 8/2006 | Shear et al. | 705/67 |
| 2001/0012913 A1 * | 8/2001 | Iliff | 600/300 |
| 2001/0037218 A1 * | 11/2001 | Kaker et al. | 705/2 |
| 2001/0042080 A1 * | 11/2001 | Ross | 707/506 |
| 2001/0051881 A1 * | 12/2001 | Filler | 705/3 |
| 2002/0151992 A1 * | 10/2002 | Hoffberg et al. | 700/83 |

OTHER PUBLICATIONS

Dialog search history_2.*

Health Management Technology, University of Nebraska Medical Center, Thomas G. Tape, Joseph H. Sisson, v17, n11, p32(4), Oct. 1996.*

Appalachia online, Hospitals and Health Networks, v17, p82, Hosi J. Cohen, Chuck Appleby, Feb. 5, 1997.*

"A Web-Enabled Framework For Smart Card Application In Health Care" Chan et al., Sep. 2001, Communications Of The ACM, 44, 9, 76, Dialog File 149, Acc. No. 02021813.

* cited by examiner

ADMISSION FACE SCREEN

| Member | ID: | m55555 | Last Name: | Gray | First Name | Jane |
| --- | --- | --- | --- | --- | --- | --- |
| | Birthdate | 11/4/50 | | ○ Male, ● Female | | |
| | Group No | A77 | | Product | Commercial | Contract No | GG234 |

| Admit Date | 11/5/200 | Today | | ☐ Related to accident or 3rd party liability |
| --- | --- | --- | --- | --- |
| Came from | Home ⇅ | | Arrived via | Auto ⇅ |
| Attending MD | Phil Byrd MD | ⇅ | | |
| Admitting MD | Susan Winters | ⇅ | | |
| | ICD9 Groups ⇅ | | Code: | |
| | ICD9 Codes ⇅ | | ☐ | |

Admit Dx ⇅

[ SUBMIT (->Census) ] [ SUBMIT (->Clinical) ] [ RESET ]

Fig 2B

Patient Smith Jane    ID: AA1111A    Admit Date 11/4/00
Female- DOB 10/15/70 Discharge Plans [home]    Admit Dx [491.3 Asthma]

Date [11/5/2000] [Chart Date Nav ◆]
Criteria [491.3 Asthma ◆] [NOTmet→Exam:Pulmonary:Chest Auscultation ◆] [Bed Location Med-Surg ◆]  Level of Care: PENDING
Additional Info [No Requests ◆]

Clinical Element [Exam ◆]
System/Group [Pulmonary ◆]
Parameter [Chest Auscultation ◆]
Finding [wheezing ◆]

-Chest Auscultation: Today: wheezing++
-Cardiac Auscultation: Today: rub++; syst ejec murmur+++
-Cardiac Palpation: Today: Prominent PMI Parameter [Chest Auscultation]    [New]
Findings [SELECT from FINDINGS LIST]
[wheezing++ ◆]  ☑ [Finding_1] [wheezing]
[Today ◆]    ○ ⊙ ○ ○    + ++ +++

[SUBMIT] [Acuity Check] [RESET]

Fig 4A

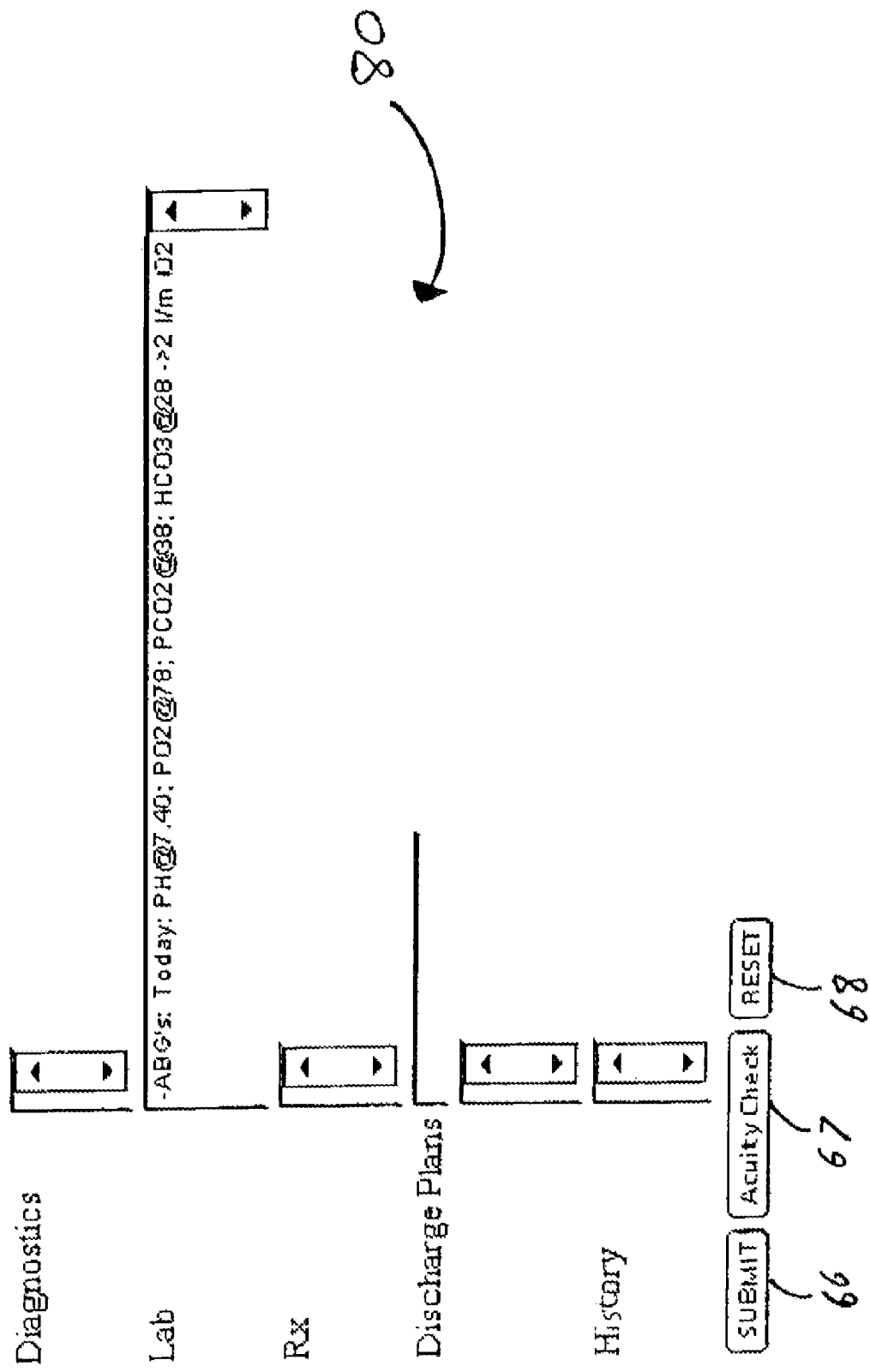

Patient Smith Jane          ID: AA11111A   Admit Date 11/4/00

Female- DOB 10/15/70         Admit Dx [↕]

Disposition |Home_____| — 71

[↕] — 72

|Home [↕]| — 73
|DME  [↕]| — 74
|E1200 wheelchair [↕]| — 75

[◄ ►] — 76, 77
- DME: E1200 wheelchair
- DME: E1000 Oxygen (tank)

[☑] |E1200 wheelchair| [New] — 78

Home Visits: |__| visit(s) over: |__| weeks / OR / |__| days /(Visit Duration |__|:hrs) — 79

Vendors
|VendorLocations [↕]| — 85
[↕] — 84
[GET]

☐ Name _____
  Address _____
  City _____ State |__| Zip |__|
Contact Last Name _____ First Name _____
  Telephone |__|-|__|-|__| Ext. |__| / Fax |__|-|__|-|__|  PIN No |__| — 86
  E-Mail Address _____

[SUBMIT] [Check for Auth] [RESET] [Discharge Order... ↕] [DISCHARGE]
   87         88            89           90                  91

Fig 5A

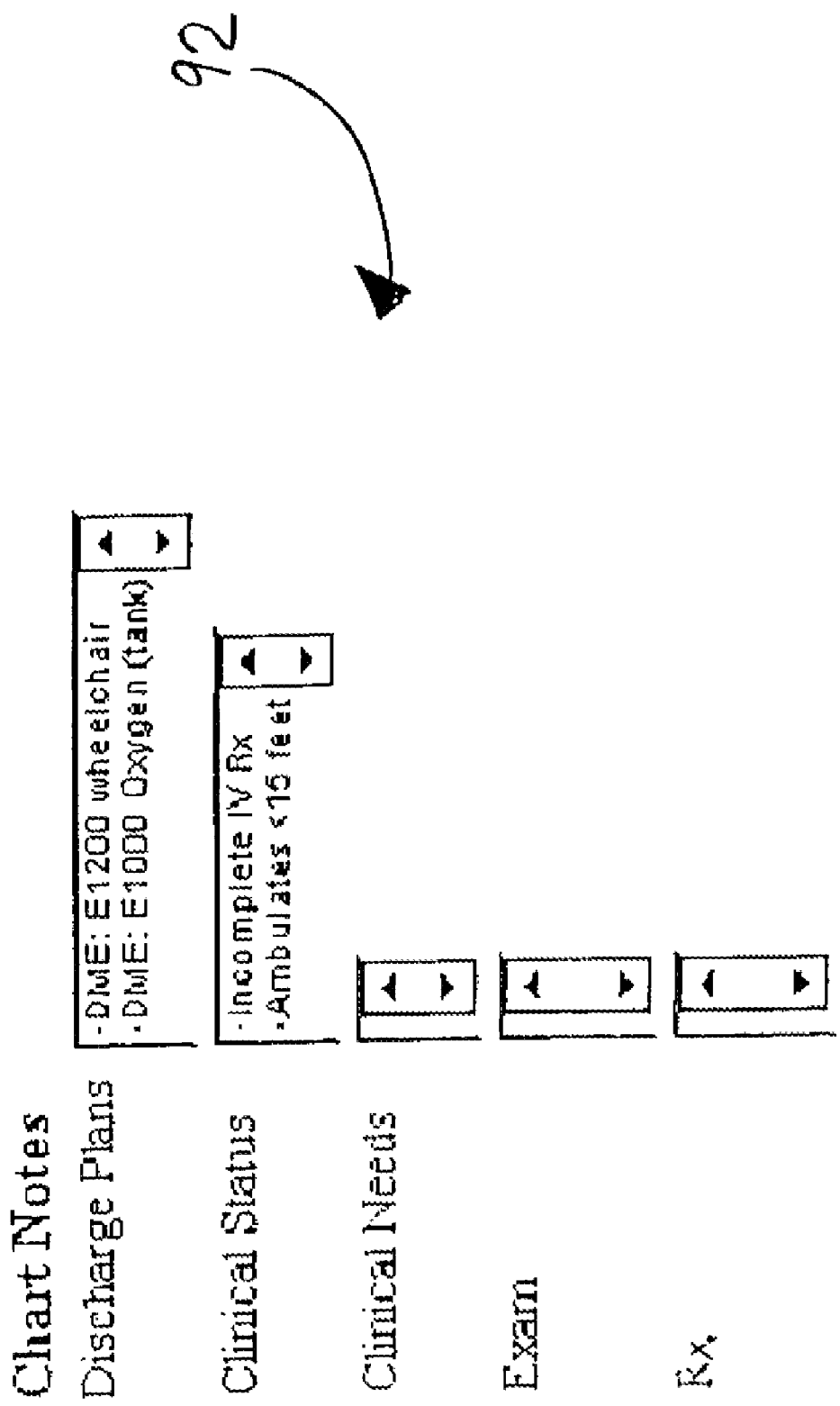

Patient West Ronald ID: cc33333c Admit Date 11/5/00
- DOB 00/00/00 Admit Dx [↕] ← 72
71 ↗

Disposition [Skilled Nursing] [↕]

Skilled Nursing [↕] ← 73
Accepting Facility Status [↕] ← 74
Needs PRI submission [↕] ← 75

-Skilled Nursing: Needs PRI submission@Sunrise Nursing Home — 76
☑ Needs PRI submission [New] ← 77
        ↑
        78

Home Visits: [ ] visit(s) over: [ ] weeks / OR / [ ] days / (Visit Duration [ ] hrs)

Vendors                    ☑ Name [Sunrise Nursing Home]        PIN No [2] ← 86
[↕]                          Address [                    ]
                             City [           ] State [ ] Zip [ ]
[Sunrise Nursing Home] [↕]   Contact Last Name [        ] First Name [     ]
        ↑                    Telephone [     ] - [     ] Ext. [  ] / Fax [  ] - [  ]
       84                    E-Mail Address [                    ]
[GET]
85 →

[SUBMIT] [Check for Auth] [RESET]    [Discharge Order...] [↕]   [DISCHARGE]
  87        88              89              90                     91

Navigator  >> SELECT THIS PROMPT TO MEET Admission: Prompt 9 + Prompt 4 e.g.

Navigator  >> SELECT THIS PROMPT TO MEET Admission: Lab: WBC + Exam: General: Temp e.g.

e.g.

Navigator  >> SELECT THIS PROMPT TO MEET Admission: Lab: WBC + Exam: General: Temp Clicking
the Navigator field resets the Element, System/Group, Parameter, and Finding pop-up button
lists to enable entry of WBC numerical value.

Fig 7C e.g.

Upon entry of the numerical value of 18000, the Navigator text field changes to display:

>> SELECT THIS PROMPT to MEET ADMISSION: General: Temp

Navigator

Fig 9A

| Brown, Jane | 09/02/05 | | | |
|---|---|---|---|---|
| 486 Pneumonia | 09/01/05 | 09/02/05 | 09/03/05 | 09/04/05 |
| Events | | | | |
| Vital Signs: Temp | | | | |
| Chest Auscultation | | | | |
| ABG's pO2 | | | | |
| WBC | | | | |
| IV Antibiotics | | | | |

|  | Meets | Not met | | Findings |
|---|---|---|---|---|
| Diagnosis | | | normal | |
| Findings | | | abnormal | |
| | | | | mildy |
| | | | | moderately |
| | | | | severely |

Additional Information Request

| Parameter | ☐ | | Date | 09/01/05 |
|---|---|---|---|---|
| Parameter | Param List | | | |
| System/Group | Group List | | | |
| Element | Elemnt List | | | |

Fig 9B

Brown, Jane ◀ 09/02/05 ▶

| 486 Pneumonia | 09/01/05 | 09/02/05 | 09/03/05 | 09/04/05 |
|---|---|---|---|---|
| Events | | | | Discharge |
| Vital Signs: Temp | | | 99.4 | |
| Chest Auscultation | Ronchi 1+ | Ronchi 1+ | | Rales 1+ |
| ABG's: pO2 | | | 72 | |
| WBC | | | 12200 | 11000 |
| IV Antibiotics | | | | |

∧∧ click for additional findings

Additional Information Request

| Parameter | ☐ | Date | 09/01/05 |
| Parameter | Param List | | |
| System/Group | Group List | | |
| Element | Elemnt List | | |

Fig 10A

Order Sheet  Date          Diagnoses  Patient Dx's ⬍   Bed unit ⬍
Patient ID  Patient Name

Orders
Orders Prompt: Orders Prompt List ⬍
Navigator   Navigator text (clickable)
Help        Help text Order        Orders List ⬍   Orders
Order Type   Type List ⬍      [Auth Symb] Date Time: Lab test frequency; stop date
Order Group  Group List ⬍     [Auth Symb] Date Time: Med, route, freq, stop date
Order Element Elemnt List ⬍   [Auth Symb] Date Time: Activity Order    Freq/Route  Frq/Rte List ⬍
              ☐

Clinical
Clinical Prompt: Clinical Prompt List ⬍
Navigator   Navigator text (clickable)
Help        Help text Finding       Finding List ⬍    Finding ☐
Parameter     Param List ⬍      Entry (New)
System/Group  Group List ⬍      Date List ⬍
Element       Elemnt List ⬍     Element (Submit)

Full Note

Fig 10B

Procedure Authorization  Diagnoses [Patient Dx's ▼]  [Bed unit ▼]

| Patient ID | Patient Name |

Procedures

Procedure ☐ [_____]  [____▼] Sched Date [_____]
Procedure   [Proc List ▼]   [Auth Symb] Procedure: scheduled date
Procedure Group [Group List ▼]   [Auth Symb] Procedure: scheduled date

Cinical

Clinical Prompt: [Clinical Prompt List ▼]
Navigator  [Navigator text (clickable)]
Help       [Help text]
Finding    [Finding List ▼]   Finding ☐ [_____] [___] [___]
Parameter  [Param List ▼]     Entry (New) [___] [___] [___]
System/Group [Group List ▼]   [Date List ▼] [___] [___▼]
Element    [Elemnt List ▼]    [Element]

(Submit)

Full Note

Fig 11A
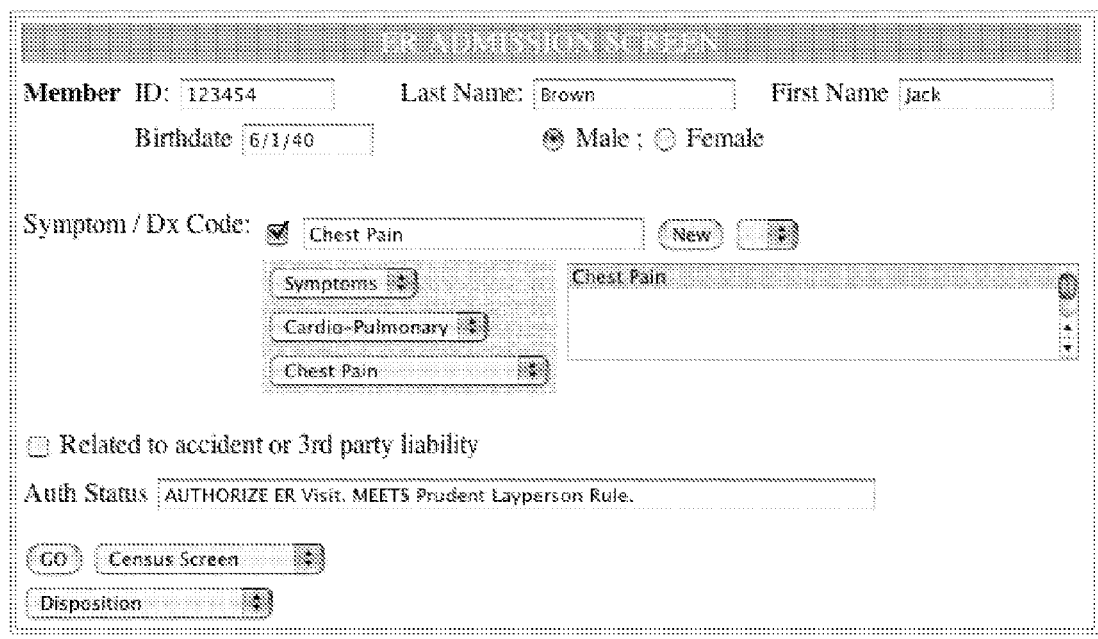
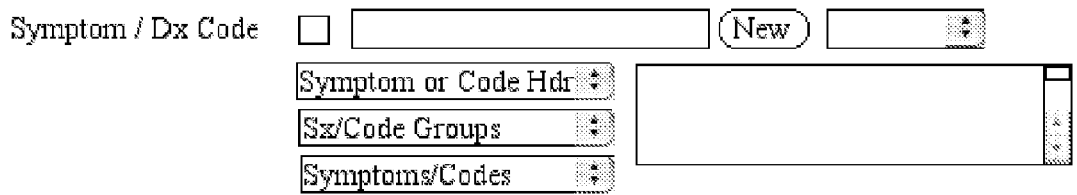

Denial Registration

Member ID [   ]   Last Name [   ]   First Name [   ]
Company [Company List ▼] [                    ]

Denied Services   Procedures
Procedure ☐ [                              ]   Sched Date
Procedure  [Proc List ▼]  [          ]
Procedure Group [Group List ▼]

Denial Reasons [Date ▼]
Denial reason ☐ [                              ]
Denial reason  [Reason List ▼]  [          ]
Denial Group   [Group List ▼]
Denial Type    [Type List ▼]

Rebuttals
[                                          ]

Fig 12B

Appeals Writer  Diagnoses [Patient Dx's ⬍]  [Bed unit ⬍]

Patient ID   Patient Name

Denial Reasons           Rebuttals

Denial reason

Denial reason 1
Denial reason 2
Denial reason 3

Rebuttals ☐

Denial reason 1
    Rebuttal 1
Denial reason 2
    Rebuttal 2

Cinical ◀ [Date ⬍] ▶   Clinical Review

Clinical Prompt: [Clinical Prompt List ⬍]

Navigator    Navigator text (clickable)
Help         Help text
Finding      [Finding List ⬍]    Finding ☐
Parameter    [Param List ⬍]      Entry (New)
System/Group [Group List ⬍]      [Date List ⬍]
Element      [Elemnt List ⬍]     Element (Submit)

Full Note

Fig 13A

Patient 2nd Opinoner

Date of Birth [    ]          ○ Male   ○ Female
Location [Outpatient ▼]      Zip Code [    ]

Your Illness

| Your Illness | ☐ [    ] [▼] |

- Problem Type [Elemnt List ▼]
- Body system [Group List ▼]
- Parameter [Param List ▼]
- Symptom/Test [Finding List ▼]

[text area]

Your Doctor's Care

| Your Doctor's Care | ☐ [    ] [▼] |

- Care Type [Elemnt List ▼]
- Group/Modality [Group List ▼]
- Parameter [Param List ▼]
- Care [Finding List ▼]

[text area]

Go [Discussion Screen ▼]

Fig 13B

Patient 2nd Opinoner Discussion Page

Your Medical Issues
Your Illness
Your Doctor's Care

Q & A
Question Prompt: [Question Prompt List]
Questions Navigator [Navigator text (clickable)]
Answer [Finding List] ☐ [____] [Date List]
[Element] ☐ Findings
Parameter [Param List]
Body system [Group List]
Problem Type [Elemnt List]

Review Answers

Discussion
References

Referrals    Other doctors in specialty
Your doctor's specialty [Specialty]
Your zip code [Zip Code]
Doctor contact Info

CLINICAL CARE UTILIZATION MANAGEMENT SYSTEM

CROSS-REFERENCE TO RELATED APPLICATIONS

This application is a continuation in part of and claims the benefit of U.S. patent application Ser. No. 09/772,394 filed in the U.S. Patent and Trademark Office on Jan. 30, 2001 now U.S. Pat. No. 7,734,480; claims the benefit and priority to Provisional U.S. Provisional Patent Application Ser. No. 60/247,246, filed on Nov. 13, 2000, entitled "UMsource Software"; and claims the benefit of Provisional U.S. Patent Application Ser. No. 60/714,968, filed Sep. 8, 2005. The disclosures and teachings of these related applications are incorporated herein by reference in their entirety.

TECHNICAL FIELD

The instant disclosure is related to data processing systems, and more specifically relates to a clinical care utilization management system.

BACKGROUND OF THE INVENTION

Clinical care rendered by physicians and other health care providers is reviewed for utilization management, quality of care, and other review or analytic functions by reviewing entities charged with these functions. Utilization management is usually performed by a health maintenance organization (HMO) or other managed care organization (MCO).

When a healthcare provider (HCP) examines and treats a patient, the HCP records the examination in a clinical chart. Under industry custom, designated personnel at the health care provider's site extract clinical information from the chart and transmit the clinical information to the reviewing entity by telephone or fax.

At the reviewing entity, personnel manually input this clinical data into an electronic form which contains one or more text fields. The information is then reviewed by one or more professional personnel to determine appropriateness of care. Determinations of the appropriateness of care are then communicated back to the health care site by phone or fax (negative determinations also require a formal letter of denial).

Because the clinical information is typically input into text fields without any formatting, the reviewing organization cannot electronically evaluate this data for appropriateness of care; instead, determinations must be made manually. As a result, determinations can be inconsistent for similar clinical situations when evaluated by the same reviewer or among multiple reviewers. There is almost no way to systematically evaluate this data among multiple clinical episodes to identify and evaluate patterns of care.

Quality of care for hospitalized patients has been nationally recognized as a major issue in health care. Review of inpatient care is sporadic and often only after an adverse event. Routine and comprehensive review of each inpatient admission and daily hospital care would improve quality of care. Physicians' care for their inpatients is not routinely reviewed proactively for quality of care. Medical therapies, endoscopies, other diagnostic testing and surgeries are not proactively re-viewed for clinical appropriateness.

Patients, particularly in-state Medicaid plans, may use the Emergency Room (ER) as their source of non-emergent primary care. Since the cost of care in an ER visit far exceeds the cost of providing care in a doctor's office, inappropriate use of the ER is a great burden to managed care organization, states, and hospitals when there is no reimbursement for the visits. Claims for ER visits may be paid on the basis of diagnosis, without review of the ER record. States generally have a law that compels payment for Emergency Room visits for illness and injuries that are thought by the average person to be dangerous, which is termed the "Prudent Lay-person Law".

Providers of healthcare services including hospitals, clinicians, durable medical equipment com-panies and companies providing parenteral medications may provide their services to patients who are members of a managed care organization (MCO). These healthcare providers may seek reimbursement for one or more services provided to a patient from an MCOs who may reject claims for payment of services. These denials of payment may be for multiple reasons, but usually are on the basis that the service or services did not meet clinical guidelines.

The healthcare provider usually has an opportunity to appeal a denial of payment with a rebuttal based on clinical rationale, which is supported by clinical information extracted from from the patient's clinical record for the denied service or services. The review and extraction of supporting clinical data is often relegated to third parties, which may be cumbersome and inexact.

The Appeals system enables providers of health care services to respond to denial of payment for services performed, including clinical care services and provision of medical equipment, usually by managed care organizations using clinical data derived from electronic clinical charts to support the clinical rationale.

Electronic clinical charts in healthcare has been a largely unfulfilled goal in this era of increasing computerization, most clinicians still using paper clinical charting to document health care. Without the buyin of clinicians, the goal of electronic clinical charting will continue to be elusive.

Reasons for resistance to using electronic charting include cumbersome labor intensive computer interfaces, requiring multiple screens, manual data entry in multiple formats, existence of multiple differing proprietary applications which may use older technology and unavailability of a uniform charting application at multiple care locations, such as hospital, office or clinic.

In this internet era of increasing patient self-education, a patient can review his or her healthcare by researching individual diagnoses and symptoms on-line. Usually, the information is not customized to a patient's specific constellation of signs, symptoms and specific medical status. Usually a patient cannot evaluate the doctor's care specifically referenced to his or her own medical status, including appropriateness of diagnostic work-up and therapies.

SUMMARY OF THE INVENTION

As may be gathered from the description above, the process for submitting and reviewing clinical records is cumbersome and time consuming. Both the HCP and the MCO dedicate personnel and other resources to the sole task of managing and processing clinical data. Accordingly, there is a need for a system that facilitates the generation and processing of clinical records, which provides sufficient data to the MCO, and which facilitate the speedy processing and authorizing of the records.

The invention provides for a centralized system for the submission and automatic processing of clinical care transactions over the Internet. The MCO contracts with a utilization management organization that employs the invention to facilitate the utilization management functions. The MCO agrees on the utilization criteria that are automatically applied by the utilization system. Health care sites are granted access to the utilization system. The health care site employs the utilization system to submit clinical transaction data. The utilization system automatically process the data and determines whether the transaction is authorized by following the agreed upon utilization criteria. The date is then further submitted to the MCO for record keeping and further review if the transaction has not been automatically authorized.

In one embodiment, the invention provides a computer implemented system for generating a medical diagnosis clinical record for submission to a MCO. The system includes a data entry interface, which facilitates the entry of data corresponding to a clinical event corresponding to the clinical diagnosis for that event. The system also includes at least one selection interface, which is adapted to facilitate the selection of at least one diagnosis. Further, the system includes a navigation module, which facilitates the identification of fields for which data should be entered. The navigation module facilitating the identification of the fields in response to the selection from the selection interface. A verification module determines the authorization level for the diagnosis by referring to at least the data in the directed-to fields. The verification module determines the authorization level prior to the submission of the record to a processing module. The invention further facilitates the submission of clinical data over Intranets and other proprietary networks.

In another aspect of the invention, there is provided a utilization management system that authorizes a diagnosis by directing the user to enter all of the required data so as to generate a sufficient clinical encounter record to evaluate the record for appropriateness of care. The system also automatically evaluates the entered data to determine an authorization level. The system includes a user interface to facilitate the submission of data to the system. The user interface is associated with a forms database that is used in generating the user screens by which data is entered. The user interface is also coupled to a navigation module that guides the user interaction with the user screens. The navigation module is associated with a selection database that provided information as to the data selections that should be available to a user. The user interface is also coupled to a verification module that is used to determine a level of authorization and criteria compliance based on the entered data. The verification module is associated with a criteria database that stores criteria rules, which are evaluated to determine an authorization level.

In another embodiment, the system facilitates the generation of encounter records that are adapted for automatic authorization processing by a remote system. The encounter records include all the data required for determining an authorization level. The encounter records further provide the data is an objective format that can be evaluated without the aid of a human operator.

In yet another embodiment, the invention provides a two step method for entering medical diagnosis data. The method includes entering a criteria into the system. The criteria corresponds to a rule required for authorizing a diagnosis. The criteria is also associated with at least one finding. Finally, the method includes entering a finding into the system.

The instant disclosure also provides an interface for entering data for the authorization of a diagnosis. The interface includes a first portion, which is adapted to facilitate the selection of a system group. The interface includes a second portion, which is adapted to facilitate the display and entry of data for the diagnosis. A display area is included within the second portion, which is displaying parameter and corresponding findings for the selected system group from the first portion. Finally, the interface includes a data entry area, which is facilitating at least the selection of findings and parameters for the system group.

The invention also provides a system where date is entered directly during the clinical event on hand-held devices that are coupled to a remote database by a network interface so as to create a clinical record of the encounter and replace paper clinical charting. In one embodiment, the hand-held devices are coupled to the utilization system by a mobile network connection.

The instant disclosure also provides an interface for the authorization of clinical care including hospital admission, acuity of level of care for inpatient hospital days, appropriateness of emergency room visits, and preauthorization of elective medical services and hospitalizations.

In another embodiment, a system can be implemented as a web based system for submitting requests for automatic authorization. A health care facility employs a web navigation interface, such as a browser, to connect to the web based system. Pages are provided to facilitate the entry of encounter date. The data is processed to provide an authorization indication before the pages are submitted.

Hospitals' financial health affect their ability to provide quality care for their patients. Hospitals' financial performance are being adversely affected with decreasing reimbursements by managed care organizations, lump sum DRG payments (Diagnosis-Related Group), the admission of sicker patients and by unlimited consumption of resources as determined by physicians as they care for their inpatients. An aspect of the invention provides an Inpatient Quality of Care system that addresses some of these issues. By reviewing orders as they are written, The Inpatient Quality of Care system enables the proactive evaluation of medical care in the inpatient setting, including evaluation of medical therapies, diagnostic work-ups, endoscopies and surgery to ensure quality care.

Importantly, hospitals' reimbursements are fixed on a per diem or DRG (Diagnosis-Related Group) bases, while physicians' consumption of hospital resources are unrestrained. Hospitals generally are unable to perform utilization management of services performed within their facilities. By reviewing orders and scheduled procedures and surgeries, the Inpatient Quality of Care system enables hospitals to have oversight over the consumption of resources within their facilities.

A computer implemented system comprising one or more computers, preferably at least two computers connected by the internet or a local area network comprising an Emergency Room system for evaluating Emergency Room (ER) visits and creating ER clinical charts for ER clinical care evaluation for health care review organizations, which: evaluates appropriateness of a patient visit by using the "Prudent Layperson Rule", and; creates an electronic clinical chart of relevant clinical data generated by one or more reasons for a patient ER visit and/or one or more diagnoses for the patient ER visit; and evaluates appropriateness of medical care for ER visit.

An electronic charting interface display, universally available on the internet, available at little or no cost to the clinician, enabling two-step "Prompt and Response Action" for rapid entry of clinical findings would be very attractive to clinicians. The costs for providing this electronic charting capability could be borne by revenue from advertisers and/or underwriters.

An electronic advisory capability for medical care and the ability to offer differential diagnoses based on the entered clinical findings in the clinical chart would further enhance clinician interest.

The Layperson Second Opinion system is a computerized system, usually on the internet, which enables a patient to evaluate a doctor's medical care based on the layperson's medical status, where the patient responds to specific questions. These questions have been formulated by inputting the layperson's medical issues for seeking medical care as well as the doctor's care.

BRIEF DESCRIPTION OF THE DRAWINGS

FIG. 4A illustrates a Clinical screen.

FIG. 4C is a continuation illustration of the chart section of FIG. 4B.

FIG. 5A illustrates a Patient Discharge screen.

FIG. 5B illustrates a chart section of the Patient Discharge screen of FIG. 5A.

FIG. 5C illustrates the Patient Discharge screen when post discharge treatment is selected for the patient.

FIG. 7A illustrates the Navigator field and its placement in a Clinical screen.

FIG. 7C illustrates an example of the new Navigator field text after entering a finding.

FIG. 9A illustrates a color-coded timeline.

FIG. 9B illustrates a timeline with text.

FIG. 10A illustrates the Physician's Orders Sheet screen display.

FIG. 10B illustrates the Procedure Authorization screen display.

Figure 11B:
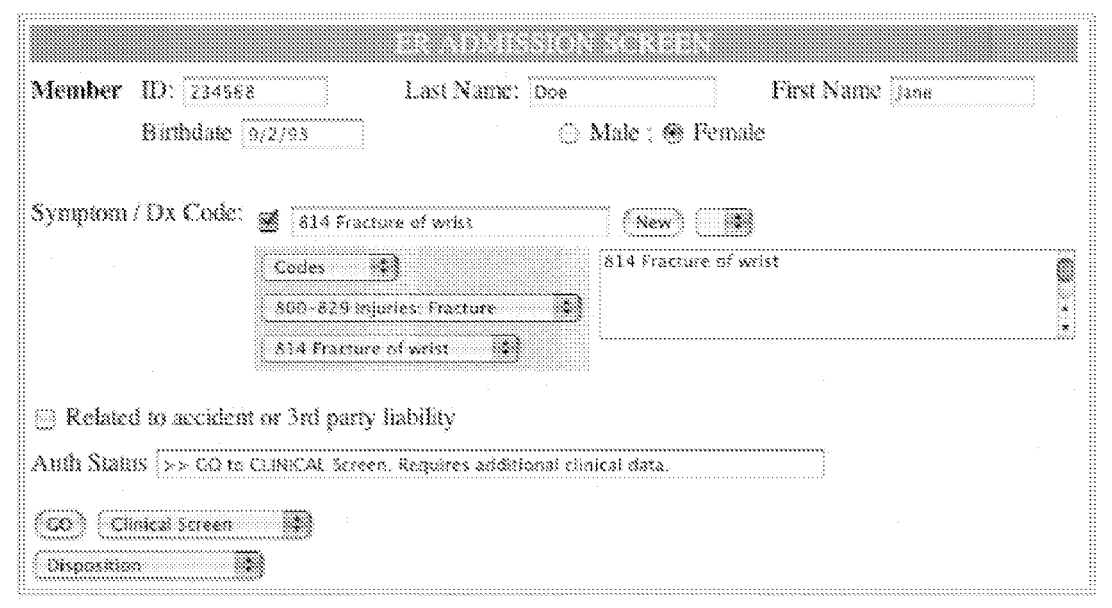
Figure 11C:
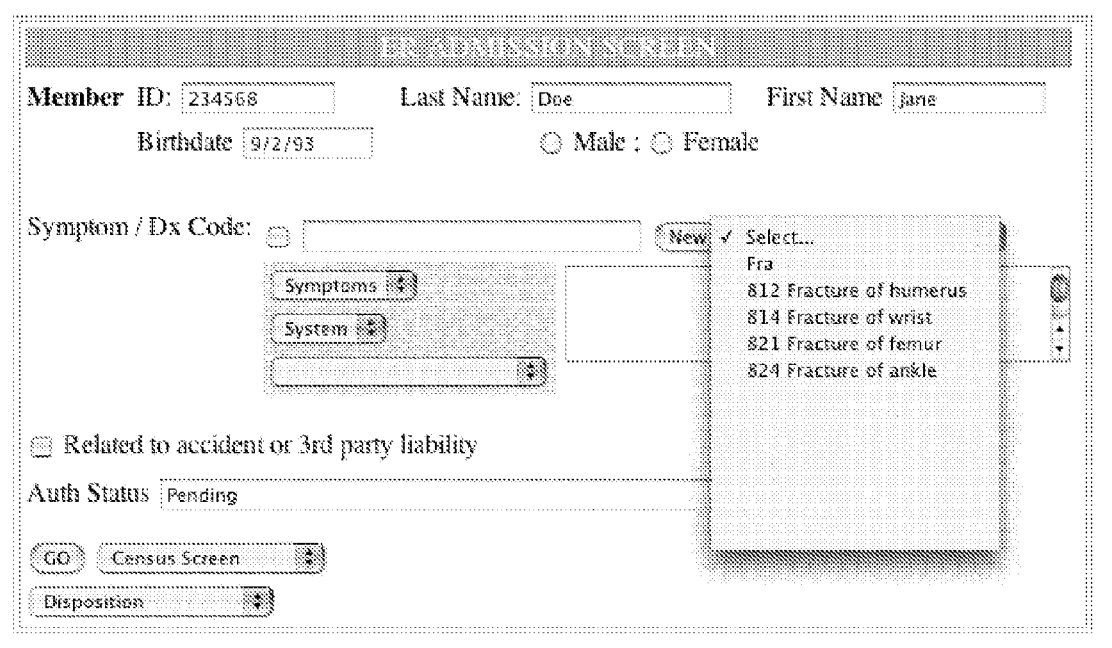
Figure 11D:
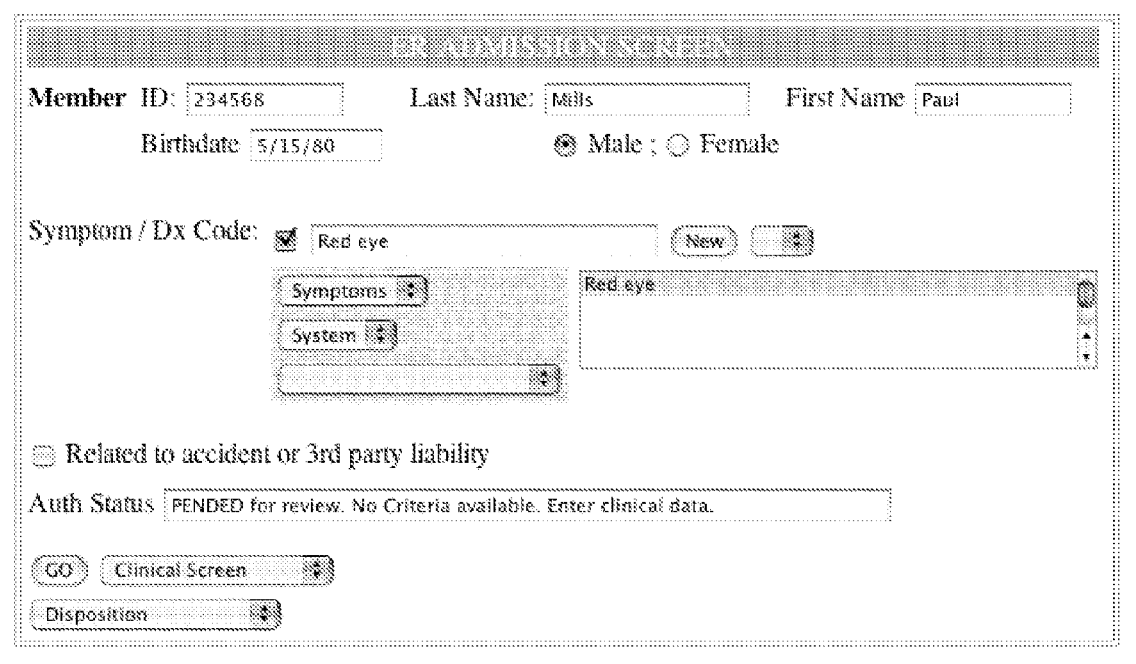

FIG. 11A illustrates the Emergency Room Face screen display, for a symptom meeting "Prudent Layperson Rule".

FIG. 11B illustrates the Emergency Room Face screen display, for a symptom requiring additional clinical information.

FIG. 11C illustrates the Emergency Room Face screen display, displaying results of a three letter entry in the "Symptom/Dx" field.

FIG. 11D illustrates the Emergency Room Face screen display, for a symptom having no criteria.

FIG. 12A illustrates the Denials Registration screen display.

FIG. 12B illustrates the Appeals Writer screen display.

FIG. 13A illustrates the Patient 2nd Opinioner Face screen display.

FIG. 13B illustrates the Patient 2nd Opinioner Discussion Page screen display.

DETAILED DESCRIPTION

The structure and operation of a utilization system in accordance with the invention will now be discussed with reference to illustrations of an exemplary utilization system. First, the structure and operation of system modules will be discussed with reference to an illustration of a system arrangement. Next, the structure and operation of the system's data entry interfaces will be discussed with reference to illustrations of user screens from a web based utilization system. Finally, the operation of the system when submitting encounter data is illustrated with reference to user screens and a flow diagram of user interaction steps.

The present discussion refers to data entry operations in the context of in the context of user interaction with the system. Such data entry operations are not limited to the entry of a textual or numerical values in an entry box but also include the selection of data from a pop-up list, the selection of a radio button from a set of buttons, the acquiescence of a user with default data that is automatically filled by the system, and a check indication in a check box. As may be appreciated, other forms of providing data are available and are intended to be encompassed within the present discussion when referring to data entry.

The present discussion refers to a "user" interacting with the system. The term "user" is intended to encompass an individual member of an organization that interacts with the system, several members of the organization interacting with overlapping portions of the system, or members of different organizations interacting with various portions of the system. Moreover, as may be appreciated, a "user" includes a computer or otherwise automated system that submits data to a processing system of the invention.

Figure 1:
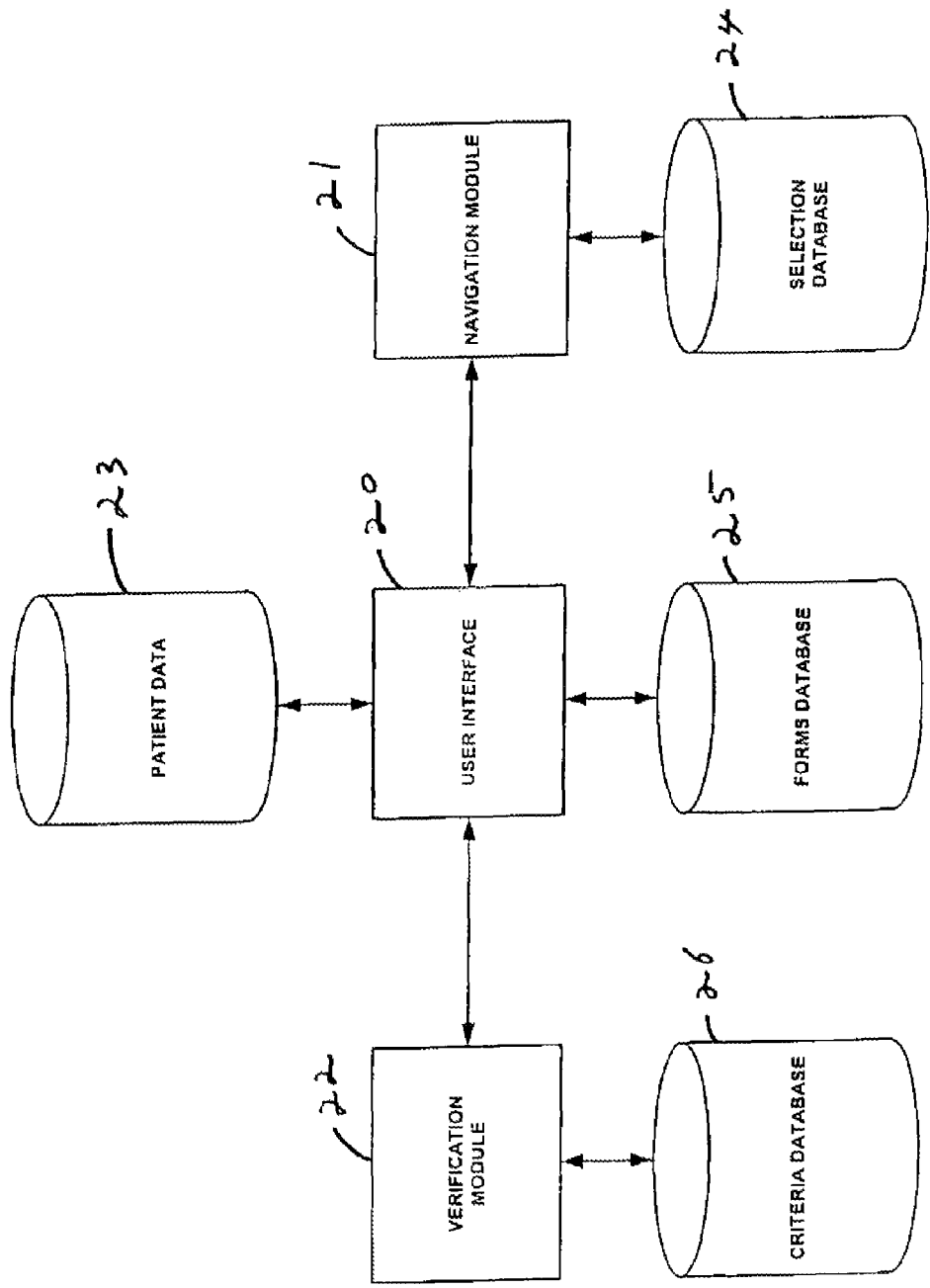
FIG. 1 illustrates the logical arrangement of modules in a utilization management system in accordance with the invention.

FIG. 1 illustrates the logical arrangement of modules in a utilization system in accordance with the invention. The modules include a user interface 20, a navigation module 21, and a verification module 22. The user interface 20 generates the user screens with which the user interacts to submit or review data. The user interface is preferably coupled to a communication link (not shown) that receives user commands and data from a network connection. In one embodiment, the communication link is an Internet connection. In another embodiment, the communication link is a local area network connection. In yet another embodiment, the communication link is a mobile, wireless, remote Internet link. In yet another embodiment, the communication link is a proprietary link.

The user interface 20 preferably facilitates the generation of user screen in accordance with predetermined screen templates and controls. The predetermined templates and controls are advantageously stored in a forms database 25. The user interface 20 is further associated with a patient data storage module 23, which stores patient data that was entered and submitted to the system. The patient data storage module 23 also stores general data relating to health care providers, health care facilities, and MCOs. The user interface 20 is operatively coupled to the verification module 22 and to the navigation module 21.

The navigation module 21 is employed to guide the user in entering data by modifying fields of the user screen in response to the user entering data that affects the navigation path available to the user. Preferably, the navigation module 21 communicates with the user interface 20 to identify when the user enters data that affects the navigation path or otherwise entails a modification of available controls. The navigation module 21 is associated with a selection database 24. The selection database 24 preferably includes data that identifies members of each hierarchal level and the logical relation between levels. Such arrangement of members and relations is illustrated in Appendix A. The example arrangement of Appendix A is for a four tier division. However, as may be appreciated, different number of tiers are used in other implementations of the invention.

The verification module 22 examines the input data to determine whether an authorization status or a criteria status should change in response to the input data. The verification module 22 is preferably associated with a criteria database 26. The criteria database 26 stores rules corresponding to criteria, which are applied to determine whether a clinical event should be authorized. The criteria are preferably in the form of Boolean rules that refer to data fields of the user screens. In one embodiment, the data for each field of the user screen is provided to the verification module 22 after the user modifies the data in the particular field. In another embodiment, selected fields of the user screen are designated to trigger the submission of data to the verification module 22.

In operation, the system provides user screens to the user by employing the user interface 20. The user screens include textual displays and data entry controls that facilitate the submission of data. Some of the screens presented to the user are static screens, whereby the same screen is provided to the user regardless of the data entered by the user. Other screens are dynamic screens, whereby the selections and data entry interfaces depend on previously entered data. In one embodiment, the dynamic screens are generated when the user interface 20 employs data from the navigation module 21 in combination with controls and form templates from the forms database 25.

The navigation module 21 preferably receives selections from the user interface 20. The navigation module 21 responds to predetermined user selections by querying the selection database 24. In one embodiment, a user selection of a criteria from a criteria pop-up list (discussed below) is received by the navigation module 21, which responds by searching for the associated element, group, parameter, and findings. In one embodiment, when the user selects a criteria, the navigation module 21 queries the database 24 for the corresponding criteria attributes for which data is required. The elements database 24 returns selections that are available to the user as a result of the newly entered data. The navigation module 21 communicates with the user interface 20 to modify the available selections in the user screen to conform to the changed navigation path. In one embodiment, an element, a group, a parameter, and a finding are automatically set in response to the selection of a criteria from a criteria pop-up list (discussed below).

The verification module 22 receives user data and determines whether the data is sufficient to authorize the clinical event or to satisfy a particular criteria of the clinical event. The rules in the criteria database 26 preferably include both rules that examine data from a single field and rules that examine data from several fields. Rules are advantageously structured to progressively determine, first, when a particular criteria is satisfied and, second, when a displayed diagnosis is authorized. Advantageously, rules are progressively applied to other diagnosis of the clinical event, when the particular displayed diagnosis is not authorized. Preferably, the rules employ Boolean functions and evaluations to define when a criterion or diagnosis is satisfied. In one embodiment, data items are combined by using Boolean operators such as AND, OR, and NOT. When the user data is sufficient to authorize a diagnosis or satisfy a criteria, the system provides a corresponding indication to the user. The indication is preferably provided prior to the user submitting the record to the utilization system. Accordingly, the verification operation is local to the user. In one embodiment, the verification is automatically prompted when the user navigates from one screen of the system to another and screen data has changed.

Preferably, the authorization criteria are set by the agency for which the record is intended. The rules are advantageously set by selecting from several sets of rules or by independently creating rule sets. As may be appreciated, different agencies may desire different rules. Thus, a user that is a customer of an agency is provided access to the system and is authorized in accordance with that agency's rules. The rules that are used for criteria and authorization evaluation are advantageously hidden from the user and are only available to authorized personal such as the MCO or the utilization system administrator.

The rule application portion of the utilization system preferably includes rules for criteria and rules for authorization levels. Criteria rules are used to evaluate whether the entered data satisfies a particular criteria that is applicable to the overall authorization evaluation. The diagnosis authorization rules advantageously refer to the results of criteria evaluations to determine the result and authorization level. The criteria rules evaluate the completeness of data in addition to evaluating whether the data satisfies a criteria. As may be appreciated, there can be more than one criteria for a given diagnosis authorization. However, at times, a diagnosis is only associated with a single criteria. The criteria preferably correspond to major symptoms as well as to the diagnosis.

In one embodiment, the criteria rule results are indicated by a message in a dialog box of the entry form. In another embodiment, the result indication is by an alert window that is provided when invalid data is entered.

In one implementation of the utilization system, the modules and databases are part of a database application written on a 4TH DIMENSION, ACI database and with HTML and JAVA Script interfaces. In another implementation, the database application is a front-end for a mainframe database. Preferably, the database application is SSL enabled to provide for transmission security over the Internet. The database includes proprietary encryption for transmission over its proprietary network.

Figure 2A:
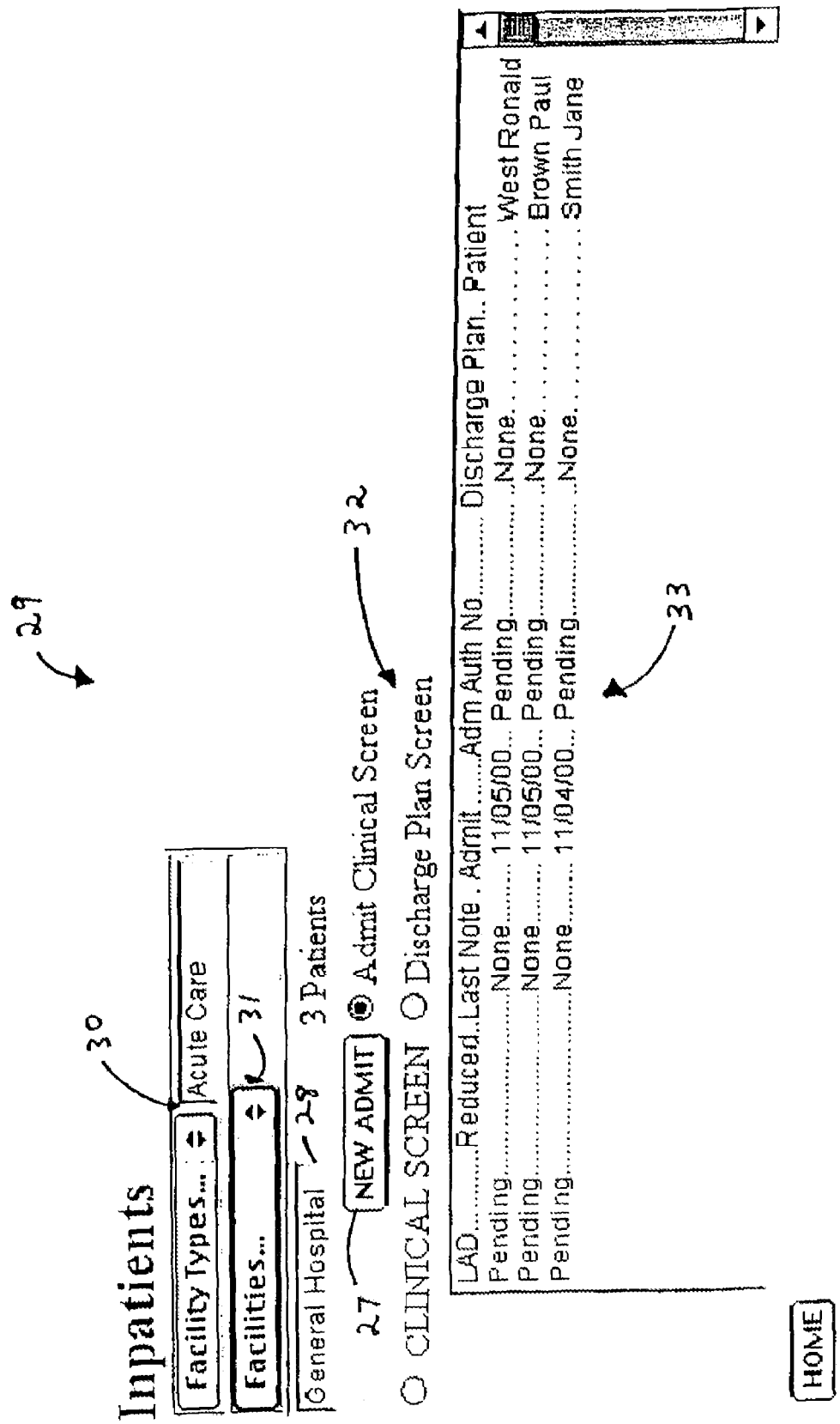
FIG. 2 illustrates an Inpatient Census screen.

FIG. 2 illustrates an Inpatient Census screen 29 of a utilization system in accordance with the invention. A facility identification portion of the screen includes a facility type pop-up list 30 to select a facility type. The facility identification portion also includes a facility pop-up list 31 to identify a facility from facilities in the network of the selected facility type. The Inpatient Census screen 29 also includes navigation buttons 32 for navigating to an Admit Clinical Screen, a Clinical Screen, and a Discharge Plan Screen. A New Admit button 27 facilitates navigation to an initial administrative patient registration screen (Admission Face screen). Finally, the Inpatient Census screen 29 includes a display box 33 that displays patient record data for the selected facility for the current date. In one embodiment, the displayed patients are all patients belonging to the MCO that are hospitalized in the facility. In another embodiment, the displayed data is for all inpatients at the facility. The display box 33 preferably includes, for each patient, the last acute day authorized, the number of days not authorized, last date that clinical data was input, admission authorization number, and discharge plan with corresponding discharge plan authorization status.

In operation, the user selects a facility type from the facility type pop-up list 30. The user then selects a facility from the facility pop-up list 31. The facility name is displayed in the corresponding display box 28. Patient data for patients that are in the facility during the default period are displayed in the display box 33. The user selects a patient record from a line of the display box 33. The user then selects one of the navigation buttons 32 to prompt the corresponding user screen for the selected patient record.

FIG. 2B illustrates an Admission Face screen of a utilization system of the invention. The Admission Face screen is used to enter patient data for a newly admitted patient. Such data includes ID number, name, gender, date of birth, admission date, attending doctor name, ICD-9 code, admission diagnosis, and any other relevant patient information.

In general, when a patient is admitted to a facility, an administrative admission record is created in the Admission Face screen. An Admission Clinical screen is then employed to submit data for creating and to review an admission clinical record. A daily inpatient clinical record is created and reviewed by employing a Clinical screen. Finally, a discharge planning record is created and reviewed at any time after admission, but preferably early in the hospitalization.

Figure 3A:
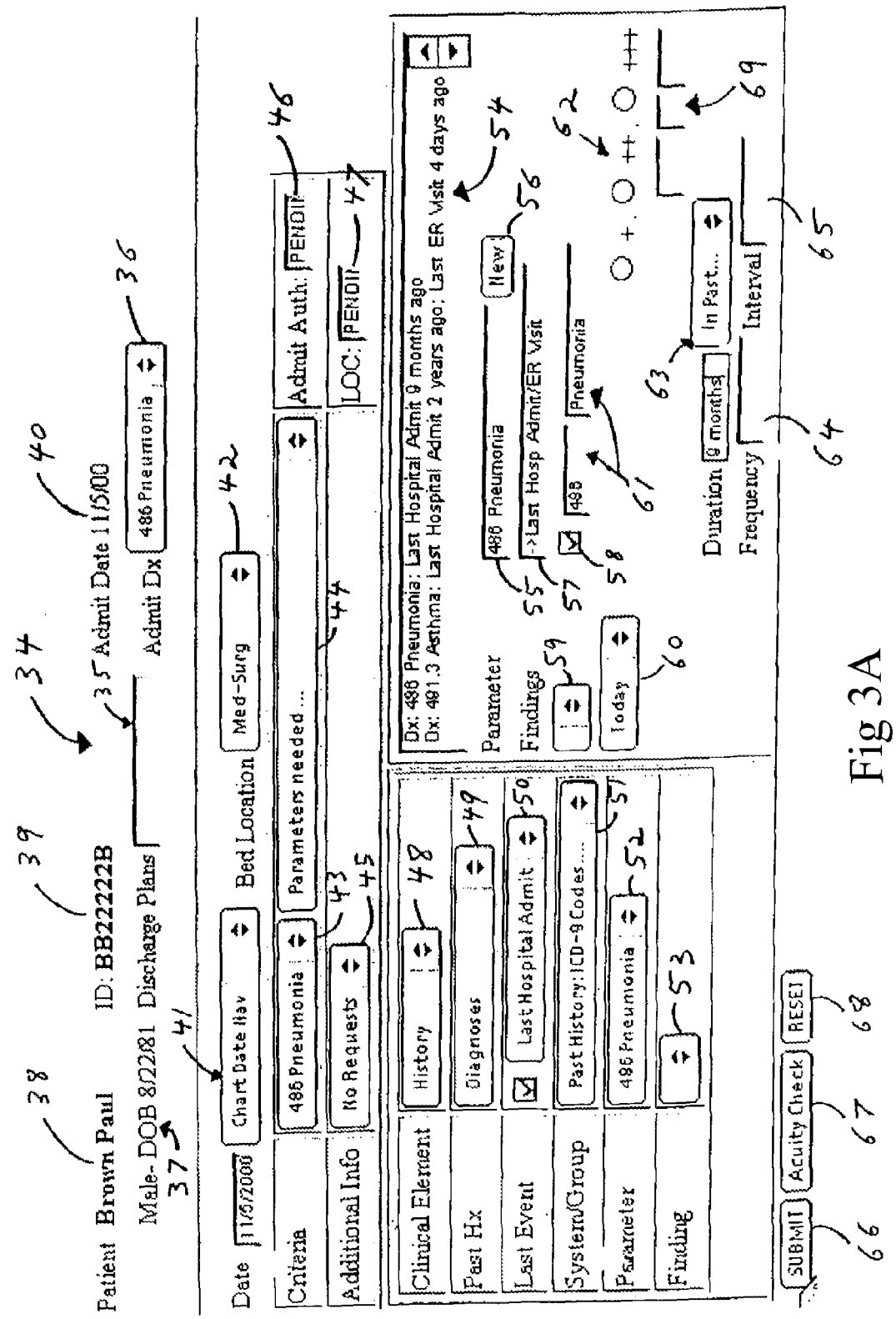
FIG. 3A illustrates an Admission Clinical screen.

FIG. 3A illustrates the Admission Clinical screen 34 of a utilization system in accordance with the invention. The Admission Clinical screen 34 is used to input the clinical data from the patient's admission exam. This includes historical data including prior surgeries, illnesses, along with the last hospitalizations and emergency room visits for these surgeries and illnesses. For example, historical data includes prior operations, prior diagnosis, prior treatments, history of symptoms, and other physiological data. The Admission Clinical screen includes a header area for displaying patient information. The header area includes a patient name 38, a patient identification number 39, a patient date of birth and gender 37, any discharge plans 35, an admission diagnosis 36, and an admission date 40. The admission diagnosis 36 is preferably set after the patient admission diagnosis is entered in the Admission Face screen of FIG. 2A. Also, the discharge plan 35 is preferably set only after the discharge plan is entered by employing the Discharge Plan screen (discussed below).

A second portion of the Admission Clinical screen is used to select a desired diagnosis for authorization and to select associated criteria. The second portion includes a chart date pop-up list 41, a Patient Location pop-up list 42, a Diagnosis pop-up list 43, a Criteria pop-up list 44, a Level Of Care display box 47, an Authorization display box 46 and an Additional Information Request pop-up list 45. The additional information request pop-up list 45 is preferably used to prompt the user for non-diagnosis related information that is manually reviewed either at the submitting HCP or by the MCO. The Diagnosis pop-up list 43 facilitates the selection of a desired diagnosis. In the context of the Admission Clinical screen 34, the entered diagnosis is an admission diagnosis. The Criteria pop-up list 44 is used to select a criteria that is associated with the desired diagnosis. The Authorization Status display 46 provides the authorization level granted in accordance with the selected criteria. The level of care display box indicates the level of care corresponding to any authorization. In one embodiment, the Criteria pop-up list 44 are preceded by a status designator such as "Needed," "Not Met," and "Met." The status designation changes in accordance with the data entered for the criteria. For example, when a criteria is fist selected, a "Needed" designation is provided. After all data is entered for the criteria, the designation changes to one of "Not Met" or "Met."

A third portion of the Admission Clinical screen 34 is employed to enter diagnosis data in a structured manner. The third portion includes several interlinked pop-up lists. An Element pop-up list 48 is employed to select a clinical element for the encounter. In the Admission Clinical screen 34, the selected element is set to History, corresponding to patient historical information. A System Group pop-up list 51 is provided to select a system group of the selected element. The system group is preferably a subgroup of the element selected from the Element pop-up list. In some context, the system group is the body system corresponding to the medical encounter. A Parameter pop-up list 52 is provided to select a parameter of the selected system group. A Finding pop-up list 53 is used to select one or more findings corresponding to the selected parameter. In the Admission Clinical screen further the parameters do not require a finding. The Admission Clinical screen includes a past history pop-up list 49 to select a medical history event type. The screen also includes A last event pop-up list 50 to select an event. Preferably, the historical data selections are from widely accepted diagnosis and procedure codes. History surgeries and diagnosis, ICD-9 code parameters and CPT-4 code parameters do not require a finding.

In operation, the uses selects either Surgeries or Past Diagnosis from the Past History (Past Hx) pop-up list 49. In one embodiment, the Surgeries are grouped, in the System/Group pop-up lists, by CPT-4 Codes. In another embodiment, the Diagnoses are grouped, in the System/Group pop-up lists, by ICD-9 Codes. Both sets of codes are issued by the AMA. Selecting a CPT-4 code or ICD-9 code in the System/Group pop-up list, enters the code with its attendant surgery or illness.

Each input Surgery or Diagnosis is concatenated with the last hospital admission episode and/or last emergency room visit, by making selections in the Last Event pop list 50, which offers a choice of Last Hospital Admit or Last ER Visit. Interval since the last event is input in the Duration field and Time Unit pop-up list 63. These last events are concatenated onto the Past Surgery or Past Diagnosis and are displayed in the Current Element scroll box 54.

The fourth portion of the Admission Clinical screen 34 includes a display portion and a data entry portion. The display portion is used to display entered parameters for the selected element in the Element pop-up list 48. For this purpose, a Current Element scroll box 54 displays the parameter data along with multiple associated findings. The entry portion includes a Parameter display box 55 for displaying the selected parameter. The Parameter display box 55 is also used as an entry box is for submitting a parameter without using the pop-up list for History and CPT-4 codes and ICD-9 codes or in preparation for submitting a new parameter. A Finding display box 57 is provided for displaying the selected finding data.

Figure 3B:
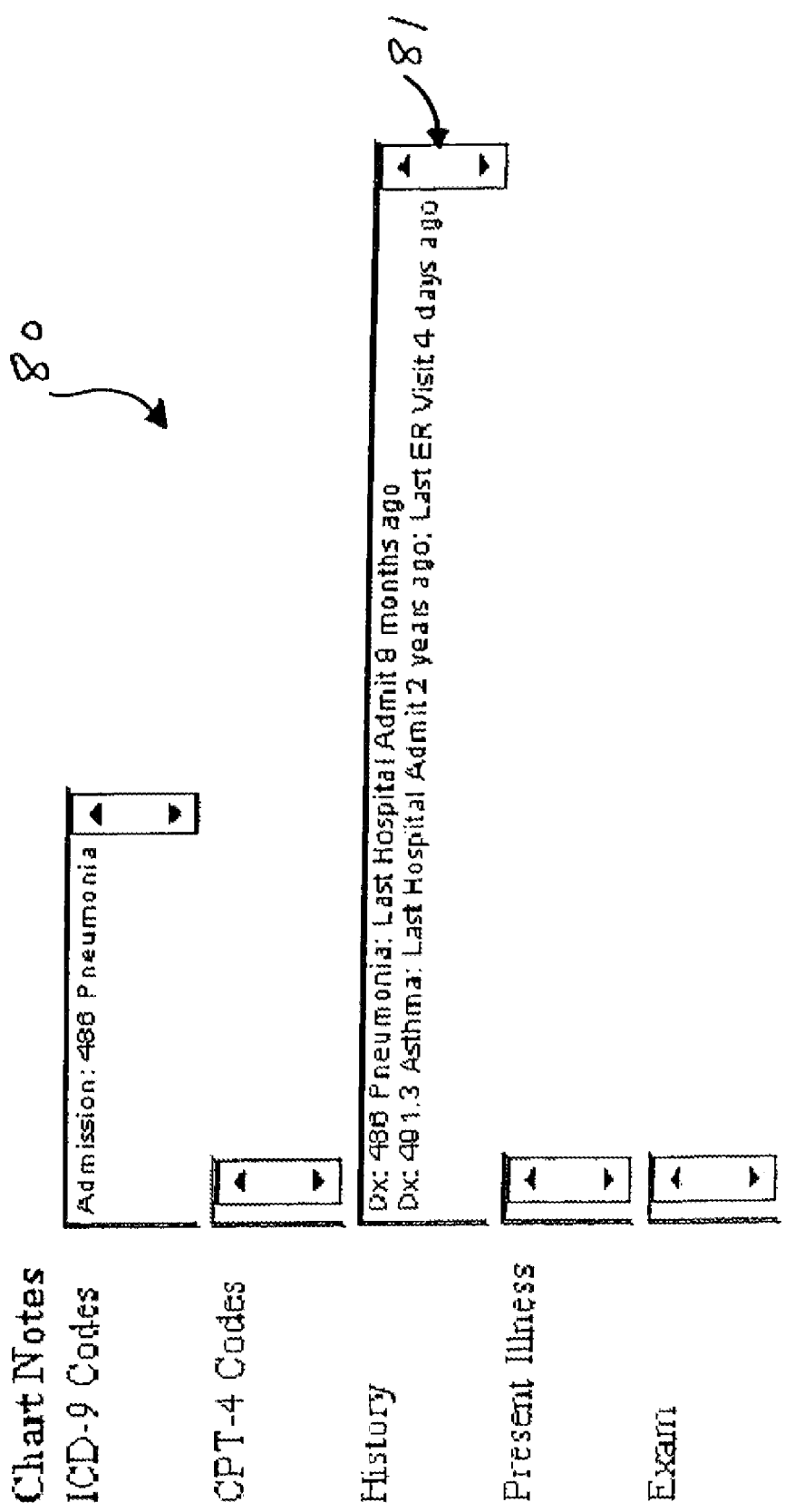
FIG. 3B illustrates a chart section of the Admission Clinical screen of FIG. 3A.
Figure 3C:
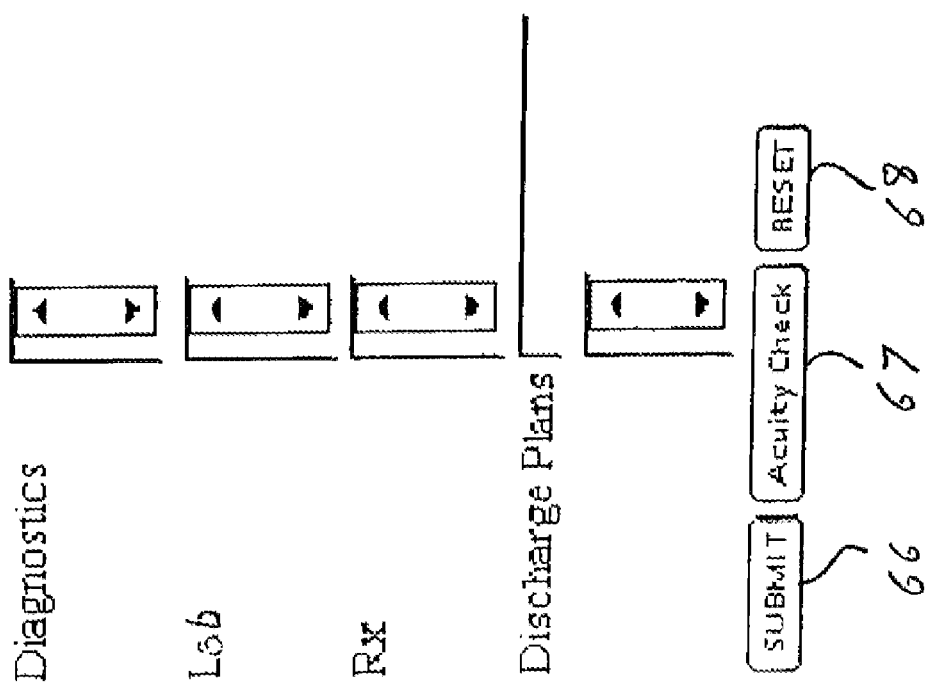
FIG. 3C is a continuation illustration of the chart section of FIG. 3B.

For most findings, selecting a finding in the Finding pop-up list 53 enters the selected Parameter with its finding on a line of the Current Element scroll box (as well as the appropriate Specific Element scroll box in FIGS. 3B or 3C). Additional findings for a Parameter are concatenated on the Parameter line after the initial finding.

For findings requiring numerical values (such as lab tests, vital signs), the Parameter and finding are displayed in the Current Element scroll box 54 only after a numeral value has been entered (see below).

Each input findings is also displayed in entry box 61 and entry box 62 and is cumulatively added to the Findings pop-up list 59. Findings not requiring numerical value (such as lab tests, vital signs) are displayed in entry box 62, while entry box 61 displays the finding instance of the Parameter (E.g. Finding—1, Finding—2). For findings requiring numerical values, the finding is displayed in entry box 61 and the clinical value is entered in entry box 62. For example, if entry box 61 displays "hemoglobin," the user would enter "16" in entry box 62 if the patient's lab tests showed a hemoglobin of 16.

Selecting one of the findings in the Findings pop-up list 59 allows modification of, or deletion of, the finding in the Current Element Scroll box. In the Admission Clinical screen 34, the Finding display box 57 is used to display the last event, which was selected from the corresponding Finding pop-up list 50. A pair of entry boxes 61 is used to display the selected parameter and finding, respectively. The entry boxes 61 are also used to marginally enter data for a finding. Entry boxes 61, 62 are also used to enter custom findings not listed in the finding pop-up list 53.

A Time pop-up list 60 is provided to select a time for the event reported. Finally, Duration and Frequency entry boxes 63, 64 are provided for submitting a duration or a frequency for the reported parameter under the Clinical Element Symptoms. An Interval entry box 65 is provided to enter an interval for the reported event. The system preferably responds to the data entry by evaluating the admission diagnosis authorization level. The evaluation is preferably by applying rules to the entered historical data. Accordingly, the user is provided with an indication of appropriateness for the selected admission diagnosis. Such indication is useful for both treatment of the patient and for submitting clinical records to the MCO.

A Chart Date Navigation pop-up list 41 displays all the dates of the patient's current hospitalization and enables the user to navigate to any of these dates to review date for the selected date. Data may be modified for any date except the admission date once the admission has been authorized. The Bed Location pop-up list 42 displays a selection of hospital locations, each which may require a different set of criteria to authorize care for the location. e.g. The standard authorization level for a patient in the hospital is "acute level of care," however the authorization for a patient in an intensive care unit would be "intensive level of care."

An Acuity Check button 67 is provided on the lower portion of the screen to prompt the verifying of data if the clinical event did not receive authorization during data input. Preferably, the system performs rule checks for the criteria associated with the selected diagnosis to determine authorization in a programmatic manner as data is being input. The acuity check preformed is advantageously more comprehensive than the automatic evaluations in response to data entry in fields of the screen. A Submit button 66 is also available for submitting the screen data to the system and navigating back to the Hospital Census screen. Finally, a Reset button 68 is available for resetting the screen selections and entries.

Preferably, the rule associated with the selected criteria is applied to the entered data after the user enters data in all required fields associated with the rule. The authorization status and the status of the criteria are modified in accordance with the result of the rule application. As may be appreciated, because an admission authorization sometimes depends on more than one criteria, a criteria can be met while the authorization status remains as pending status.

FIG. 4A illustrates the Clinical screen 70 of the utilization system. The Clinical screen 70 includes the same header portion as the Admission Clinical screen 34. The Clinical screen 70 also includes the same second portion as the Admission Clinical screen 34. The third portion of the Clinical screen 70 is different from that of the Admission Clinical screen 34. In the Clinical screen, the selection of a criteria from the Criteria pop-up list 44 prompts the navigation of the Element, System Group, and Parameter pop-up lists 48, 51, and 52 to the applicable data for the selected criteria. The user then selects a finding from the Finding pop-up list 53. If data is required for a finding, the user enters the data in the entry portion of the screen. The entry boxes a first box that is used as a placeholder when data requires only a single entry field, and a second box to enter data. The findings available in the findings pop-up list 59 of the data entry portion are the findings that have been previously entered for the parameter. Furthermore, in the data entry portion Finding pop-up list 59, each finding is preferably followed by the associated data for the finding. In the illustrated example, the severity indication from the radio control box is provided following the finding "wheezing." Preferably, when the "Exam" element is selected from the Element pop-up list 48, all possible findings for the particular exam are displayed in the Finding pop-up list 59 of the display portion, whether selected or not, along with any entered values.

The display portion also includes a check box 58 to delete the selected finding from the findings associated with the parameter in the Element scroll box 54. In one embodiment, the data entry portion includes a Severity Selection radio-type control 62. In other embodiments, the data entry portion includes other control boxes as may be required in accordance with the data type assigned to the selected finding. Preferably, selecting an element from the Element pop-up list 48 brings up the element data already entered in the current element scroll box 54. The parameter or finding are advantageously not displayed until minimum data is entered. Accordingly, findings that require a value, in addition to a selection, are not displayed in the current element scroll box 54 until the corresponding value is entered.

FIGS. 3B and 3C and FIGS. 4B and 4C illustrate chart notes portions 80 of the Admission Clinical screen 34 and of the Clinical screen 70, respectively. The illustrated portions 80 are preferably visible to the user when the screen is scrolled down by employing scrollbar controls of a browsing interface. The chart notes portion 80 includes a separate scrollbox display for each element available to the user in the corresponding screen. Each display scrollbox includes the data that was entered for the corresponding element. Preferably, each display scrollbox includes a control whereby when the user selects a data line from the scrollbox, the corresponding data is made available in the entry portion of the corresponding screen and is displayed in the current element scrollbox 54. Accordingly, the user is able to browse the data that was entered for each element and to modify the entered data by selecting the data display line in the chart notes portion 80.

FIG. 5 illustrates a Discharge screen 71. The Discharge screen 71 is used to set patient discharge actions and other post-encounter actions. The disposition screen 71 includes a first portion that displays patient information. The first portion is the same as the first portion of the Clinical screen 70. A second portion of the screen includes a Disposition Location pop-up list 73. The disposition location is the facility or service that the patient requires after discharge. The simplest and most common discharge plan is disposition to home with no post discharge support services. However, many patients require various support services to maintain wellness post discharge at home, or may be discharged to another inpatient facility that provides services at a lower level of care.

A third portion of the screen includes an Item Type pop-up list 74, and a collection of follow up action check boxes 79. The Item Type pop-up list 74 includes a DME entry to select Durable Medical Equipment. The Item pop-up list 75 is used to select an item the item type previously selected. Such Item selections include equipment and treatment plans, depending on the applicable discharge plan. A fourth portion of the screen is used to provide vendor information for the selected item. The fourth portion includes a Vendor Location pop-up list 85, and a Vendor pop-up list 84. A scroll box 72 for entering anticipated clinical status on discharge is also provided. In one embodiment, the selected item and findings for the discharge status conform to a discharge rule. The disposition data in the Disposition pop-up list 72 is preferably provided as part of the header on the Clinical Screen to and on the Admission Clinical screens 34. Preferably, once a vendor is selected, the display area 76 updates with the entered item data. The Discharge screen 71 is also used to enter a discharge plan for a patient.

In operation, the user selects a disposition location for the patient. The location is home, or one of several other post treatment facilities. After selecting a location, the user is presented with corresponding pop-up list entries. For example, when a facility is selected as the location, available post-discharge treatments are provided in the Item pop-up list 74. In one embodiment, the utilization system automatically reviews the discharge plan to ensure that the plan is appropriate to the patient's level of functioning and expected needs at discharge. In another embodiment, the discharge plan is submitted to the MCO for manual review.

FIG. 5B illustrates a chart area of the Discharge screen. As discussed above with reference to FIGS. 3B, 3C, 4B, and 4C, the chart area is a bottom portion of the corresponding screen, which includes individual display scrollboxes for elements of the screen. In the context of the Discharge screen, the chart area 92 includes scrollboxes for Discharge Plans, Clinical Status, Clinical Needs, Exam, and Rx.

FIG. 5C illustrates a Discharge screen 71 with data selections for a post-discharge treatment facility. The selected disposition from the Disposition Location control 73 is Skilled Nursing. The item selected for the disposition is of Needs PRI submission. The vendor location of Nyack is selected. The vendor of Sunrise Nursing Home is selected from the vendor pop-up list. As discussed above, the vendor details are displayed after the vendor is selected from the vendor pop-up list.

Figure 6:
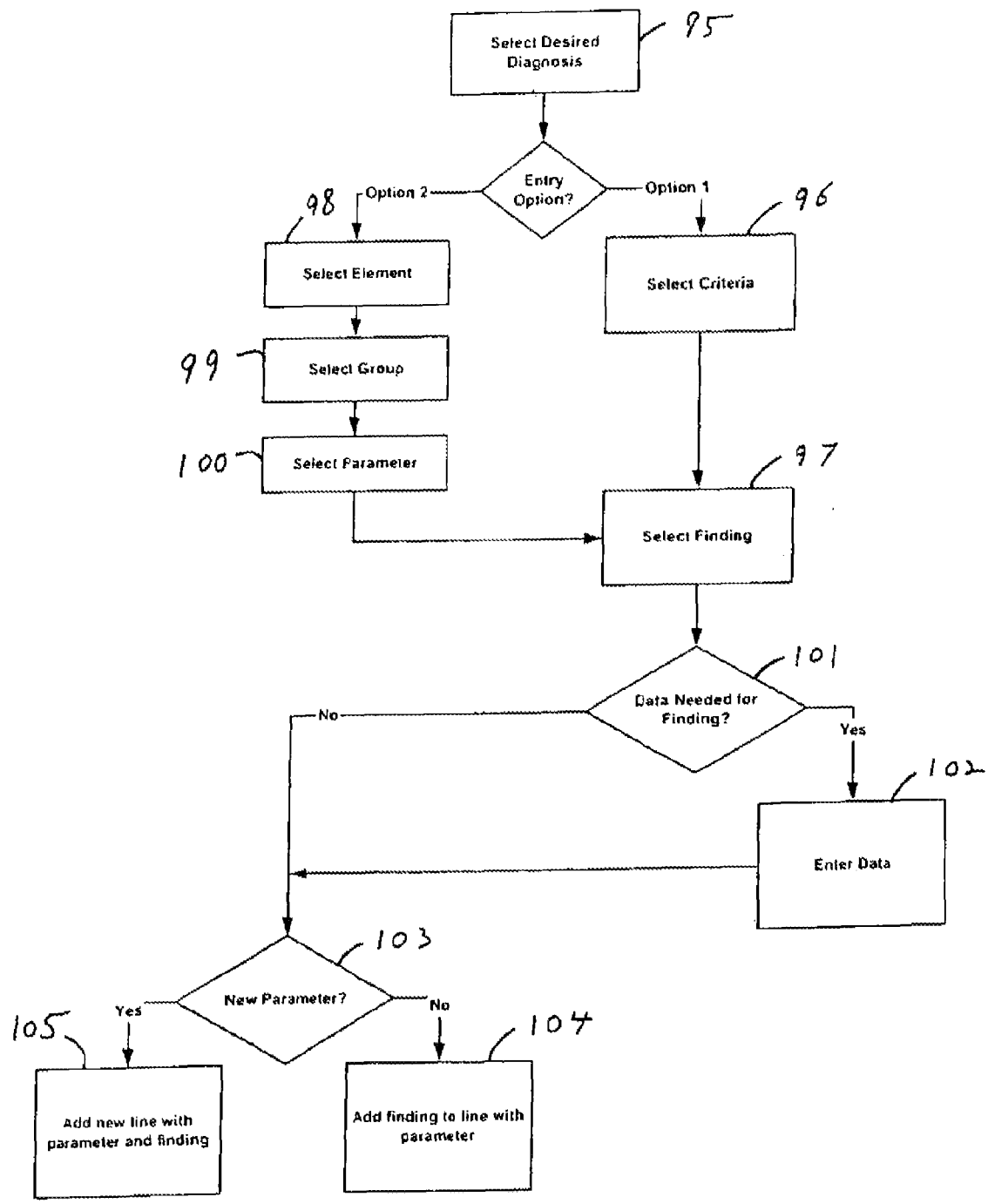
FIG. 6 is a flow diagram illustrating a process for entering diagnosis data in accordance with the invention.

FIG. 6 is a flow diagram illustrating the process for submitting medical encounter data in the Clinical screen 70. The user starts by selecting a diagnosis from the diagnosis pop-up list 43 (step 95). The user has two options in submitting encounter data to the system. A first option is a two-step entry procedure. First, the user selects a criteria from the criteria pop-up list 44 (step 96). The criteria selection results in the automatic population of the element, system group, and parameter pop-up lists 48, 51, and 52. The user then selects from the Finding pop-up list 53 (step 97).

Alternatively, the user employs the second entry option, which is to progress through the hierarchal pop-up lists in the third portion of the Clinical screen 70. The user selects an element from the Elements pop-up list 48 (step 98). The system searches for groups that are associated with the element. Preferably, the navigation module 21 searches the selection database 24 for associated groups. The navigation module 21 then identifies the groups that should be made available in the System Group pop-up list 51. The user then selects a system group from the System Group pop-up list 51. The system then employs the navigation module 21 to identify the parameters associated with the selected system group. The associated parameters are then made available for user selection from the Parameter pop-up list 52. The user selects a parameter from the Parameter pop-up list 52 (step 100). The system then employs the navigation module 21 to identify the data range and format for findings that are available for the parameter. The findings, including the associated data ranges and formats are employed to provide the user with a selection and entry interface for findings. The user then selects a finding from the Findings pop-up list 53 (step 97).

The system then determines if additional data is required for the finding (step 101). If additional data is required for the selected finding, the user employs the provided interface to enter the data (step 102). For example, when the needed data is a severity indication, the user selects a severity from a radio control button.

After receiving all the required data for the selected finding, the system adds the selected finding to the findings associated with the selected parameter. The system determines if the parameter is a new parameter that is not in the parameter list for the current element (step 103). If the parameter is not a new parameter, the finding and any associated data is added to the corresponding line of the parameter list (step 104). If the parameter is a new parameter, the parameter is added as a new line to the parameter list, along with the corresponding finding and any associated data (step 105). In one embodiment, the selected finding, along with its associated data, if any, is added to a display scrollbox where all findings for a parameter are provided on one line of the display box. The system then preferably stores the user entries and proceeds in accordance with user selections to authorize the record or format the record for submission to an authorization agency.

In another embodiment, the data is directly entered by a doctor or a treating nurse. The data is entered by employing a mobile personal data appliance such as a PALM computing device. The mobile device interacts with the server and specially configured user screens to enter patient and treatment data, as discussed above. Therefore, there is no need to use paper data recording that are later entered into the utilization server by an operator.

Preferably, the screens of the utilization system are web page screens. The controls are common web page controls, as is known. The data is preferably provided to the authorization agency as part of digital reporting and records. In one embodiment, a text file is transmitted to the agency on a weekly basis.

In other embodiments, the MCO employs the system only for gathering data from clients without the automatic evaluation of authorization status.

In an alternative embodiment, a clickable Navigator field is provided in the Clinical screen displays of the Clinical Care Utilization Management System. In this regard, a diagnosis for a patient clinical encounter may have multiple criteria which are displayed in the Prompt pop-up button list of the Clinical screen displays. There may be multiple combinations of criteria prompts (prompt subsets) that may allow the diagnosis to meet criteria, so that a user may not have to respond to all prompts. The Navigator field allows the user to save time and energy selecting and responding to prompts in differing prompt subsets.

The Navigator field is a clickable text field in each of the Clinical screen displays of the Clinical Care Utilization Management System which:

displays text that informs the user of criteria prompts that should be selected, and, is based on the clinical findings already entered, and; enables the user to select the first prompt in the text field to be automatically selected; by clicking anywhere over the Navigator text field, thereby; populating and making a selection in the Element, System/Group and Parameter pop-up button lists, thereby populating the Finding pop-up button list for user selection of a finding, or: making a selection of a finding which enables a user to enter a numerical value.

The Navigator field text may change dynamically after each finding is entered. The new text depends on the entered finding, no longer displaying the prompt for the finding just entered. The new text may display the remaining prompts displayed prior to entry of a finding, or a new subset of prompts. The new text may be blank.

Clicking the Navigator field expedites the two-step "Prompt and Response Action" by replacing the first step's manual selection of a criteria Prompt over the Navigator field, with:

1) click the Navigator field, and
2) select the finding (or enter the numerical value of a selected finding).

The user may elect to manually select a prompt rather than click the Navigator field to automatically make a selection. FIG. 1A illustrates the Navigator field and its placement in a Clinical screen. FIG 1B illustrates an example of the Clinical screen after clicking Navigator field. FIG 1C illustrates an example of the new Navigator field text after entering a finding.

In an alternative embodiment, the instant disclosure provides a computer implemented system of downloading clinical charts from the UM server computer to a user's computer network in Excel™ spreadsheet format in the Clinical Care Utilization Management System. The information in a patient's clinical chart created on a Clinical screen on a user's computer is downloaded and stored on the server computer. A user can download, review and store the clinical chart on the user's own computer system, often for use in the user's own proprietary electronic healthcare system. A user can review the clinical notes of multiple encounters in one screen display. That is, the user can review the clinical notes for a patient's entire hospitalization, or for the clinical notes for the patients recent office visits. The system allows serially viewing of each clinical note. A medical reviewer, such as a hospital administrator or chief of service, may want to review the clinical charts of multiple patients. Again, the system allows serially viewing of each clinical note.

The system allows downloading clinical charts to a user's computer system of clinical charts created in the Clinical screens of the Clinical Care Utilization Management System which, displays the clinically formatted chart notes in Excel™ spreadsheet format, whereby: a clinically formatted clinical note for a single patient clinical encounter is displayed in one cell of an Excel™ spreadsheet, and; multiple encounters for a single patient can be displayed in the cells of one row in an Excel™ spreadsheet, where; each column can display a cell for a single encounter, and; where each cell can contain the formatted clinical note of one encounter, where; the first several cells of the row display the patient's identifying and non-clinical information such as name, ID number and demographics, and; multiple encounters for multiple patients can be displayed in the cells of multiple rows in an Excel™ spreadsheet, where each row's cells display the clinical notes of a single patient, and; the data in the Excel™ spreadsheet is available for storage in the user's computer system via importation by a user's proprietary computer application, or; the data in the Excel™ spreadsheet is available for storage in a user's computer system by a user's cut and paste action into a user's proprietary computer application's fields, or; the data in the Excel™ spreadsheet is available for storage in the user's computer network via importation by a proprietary computer application, or; the data in the Excel™ spreadsheet is available for automated storage in the user's computer network via customized computer code, and; the data stored in the user's computer network may be displayed in the user's proprietary computer application in clinical chart format.

Alternatively, the clinical notes of multiple patients can be displayed in one row of the Excel™ spreadsheet, with the cells containing each patient's clinical notes are preceded by cells identifying the patient. FIG. 2 illustrates an example of downloaded clinical notes for multiple patient encounters in Excel™ spreadsheet format.

In an alternative embodiment, the system allows reviewing of multiple clinical encounters in a timeline format, whereby the clinical findings of clinical charts multiple encounters can be reviewed and compared in one computer display, and a medical reviewer can request additional clinical information, base on review of the timeline.

In reviewing a patient's health care, a medical reviewer or clinician may encounter large amounts of clinical information present in multiple separate locations, of differing utility and find it cumbersome to follow the clinical course of the patient. This is true for both paper and electronic medical records.

e.g. A review of a patient's hospitalization may require the review of an emergency room note, an admission note, notes for each day of hospitalization, laboratory data, diagnostic tests, all re-corded in different portions of the hospitalization.

e.g. A review of a patient's outpatient clinical course over a defined interval such as 6 months or a year, may require the review of multiple office notes.

Clinical notes displayed in the Clinical Care Utilization Management System are displayed for a single encounter, or, when downloaded in Excel™ spreadsheet format, are displayed for multiple notes in clinical chart format. Comparing clinical findings for multiple encounters is cumbersome. There is no designation of individual findings meeting individual criteria.

Graphic display of large amounts of information facilitates the comprehension of the displayed data much more readily than text display.

A graphic display comprising a timeline display of large amounts of clinical data facilitates the comprehension of the clinical data. The large volume of data may be a result of reviewing multiple clinical encounters, or of a single clinical encounter where there is ongoing change in patient status and therapy, such as in the emergency room.

The system displays clinical findings of multiple patient clinical encounters in timeline format, and comprises; a computer screen display, in which: each encounter is displayed in a column, and; one clinical item, usually a parameter or a finding, is displayed at the start of a timeline row, and; each cell may depict one or two separate color code systems comprising: a first color code system depicting whether the finding or findings are within normal limits, or by the degree of abnormality, and/or; a second color code system which may simultaneously, or separately, depict whether the finding or findings for a cell meet a criterion, and; text that displays the finding or findings, and where; a cell which depicts multiple findings may display the text for each finding by a user click, and; a timeline can display a notation of a clinical event: e.g. surgical or endoscopic procedure, or e.g. placement on a ventilator; a third color code system simultaneously may depict whether each patient encounter is medically appropriate by meeting criteria, and where; timeline rows may be established by clinical-derived criteria, such as a diagnosis or the reason for the encounter, prompt parameters, or; timeline rows may be established by the entered clinical findings in the clinical chart for the encounter, or; where a medical reviewer may add one or more rows, usually by selecting an item in a pop-up button list, and; where a medical reviewer may delete one or rows in the timeline, and; where there is more than one reason or diagnosis for a patient encounter, a reason or diagnosis can be selected in a pop-up button list, possibly changing the second color code system display for each cell, and; where a medical reviewer may select one encounter in the timeline to review the findings of that encounter in clinical chart format, or; where a medical reviewer may select alternate encounter dates for display when the number of encounters exceed the number of columns displayed.

In another embodiment, the timeline is for a single encounter where the patient's clinical status and therapies may be changing and where; each column of the timeline is the time of entry of a clinical findings, and a medical reviewer may select alternate encounter time for display when the number of entry times of findings exceed the number of columns displayed.

A system whereby a medical reviewer may enter requests for additional clinical information for one or more patient clinical encounters, by: clicking on a portion of the timeline, or selecting an item from a pop-up button list, or by manually entering the request.

FIG. 3A illustrates a color-coded timeline for multiple days of a hospitalization for a patient with pneumonia. A legend for color codes is displayed. An area is displayed for reviewer request for additional information.

FIG. 3B illustrates a color-coded timeline with text for multiple days of a hospitalization for a patient with pneumonia. An area is displayed for reviewer request for additional information.

A computer implemented system comprising one or more computers, preferably at least two computers connected by the internet or a local area network enabling inpatient review of medical care by proactively reviewing doctors' orders as they are written and requiring preauthorization of scheduled inpatient procedures.

A computer implemented system comprising one or more computers, preferably at least two computers connected by the internet or a local area network for reviewing the medical care for hospitalized patients comprising: an Inpatient Quality of Care system comprising: an Order Sheet Evaluation system, and; a Procedures Preauthorization system.

The Order Sheet Evaluation system comprises: An Admission Face Screen display on a user computer, which; for recording a patient's admission to a hospital, and; enables the entry of a patient's identifying and demographic data, and; enables the entry of one or more diagnoses responsible for the admission.

A Physician's Orders Sheet display on a user computer, comprising; an Orders section for entry of physicians' orders, and; a Clinical section for entry of clinical findings, which; requires no scrolling of screen for user interaction, and; enables real-time, concurrent, automated evaluation of physician orders as each order is electronically entered on a user computer, usually connected to a server computer, and provides the physician user with real-time feedback as to the medical appropriateness of each order, based on: diagnoses and clinical findings already entered into the electronic clinical chart for the encounter, including tests, procedures and therapies already performed and; if additional findings are needed by the system to evaluate medical appropriateness of an order the, Clinical section displays: criteria prompts which are populated in the Prompt pop-up button list to prompt the user to enter the additional findings into the clinical chart needed to evaluate the order, and; a clickable Navigator field text displays text describing the Prompts which; when clicked, selects the first Prompt in its displayed Navigator field to select this Prompt which then: sets the Element, System/Group, Parameter and Finding pop-up button lists in response to the criteria prompt selection, and; populates the Findings list for user selection, or, for numerical findings, is selected to allow user numerical input.

Selections in the pop-up button lists can be made manually, and; findings can be selected or entered manually.

The Physician's Orders Sheet display Orders section displays each entered order in the on-screen scrollable order sheet, displaying the date and time of the entry, the order, and a stop date, if relevant.

FIG. 4A illustrates the Physician's Orders Sheet screen display comprising: The Orders section which comprises: An Orders Prompt pop-up list which is populated by patient's diagnoses as well as the patient's current medical status as determined by multiple factors including previous orders, clinical findings, medical therapies and procedures already performed; a clickable Navigation text field functions allows automatic selection of prompts; an interactive cascading set of pop-up button lists which function to offer an Order list selection in the Order pop-up button list for entry into the order sheet; a display of entered orders each entered line displaying: a symbol denoting the appropriateness of the order; the date and time of the order entry, and; a stop date for the order, if appropriate.

The Clinical section which comprises: An interface which is similar to the Clinical screen displays in the Clinical Care Utilization Management System. The Physician's Orders Sheet screen display is also available for electronic and manual review by medical reviewers and hospital administrators. Orders which are deemed as not clinically appropriate are flagged for referral to hospital administration's physician advisors for interaction with the physician writing the orders.

In another embodiment, The Physician's Orders Sheet screen display is also available to a utilization management organization for electronic and manual review by medical directors. Orders which are deemed as not clinically appropriate are denied.

A Procedure Preauthorization system comprises: a Procedure Authorization screen on the user machine a section for entry of diagnostic and surgical procedures, and; a section for entry of clinical findings, which: functions in a manner similar to the Physician's Orders Sheet screen display, evaluating procedures instead of orders.

In another embodiment, the Procedure Preauthorization system is available for preauthorization of outpatient services.

Figure 4B:
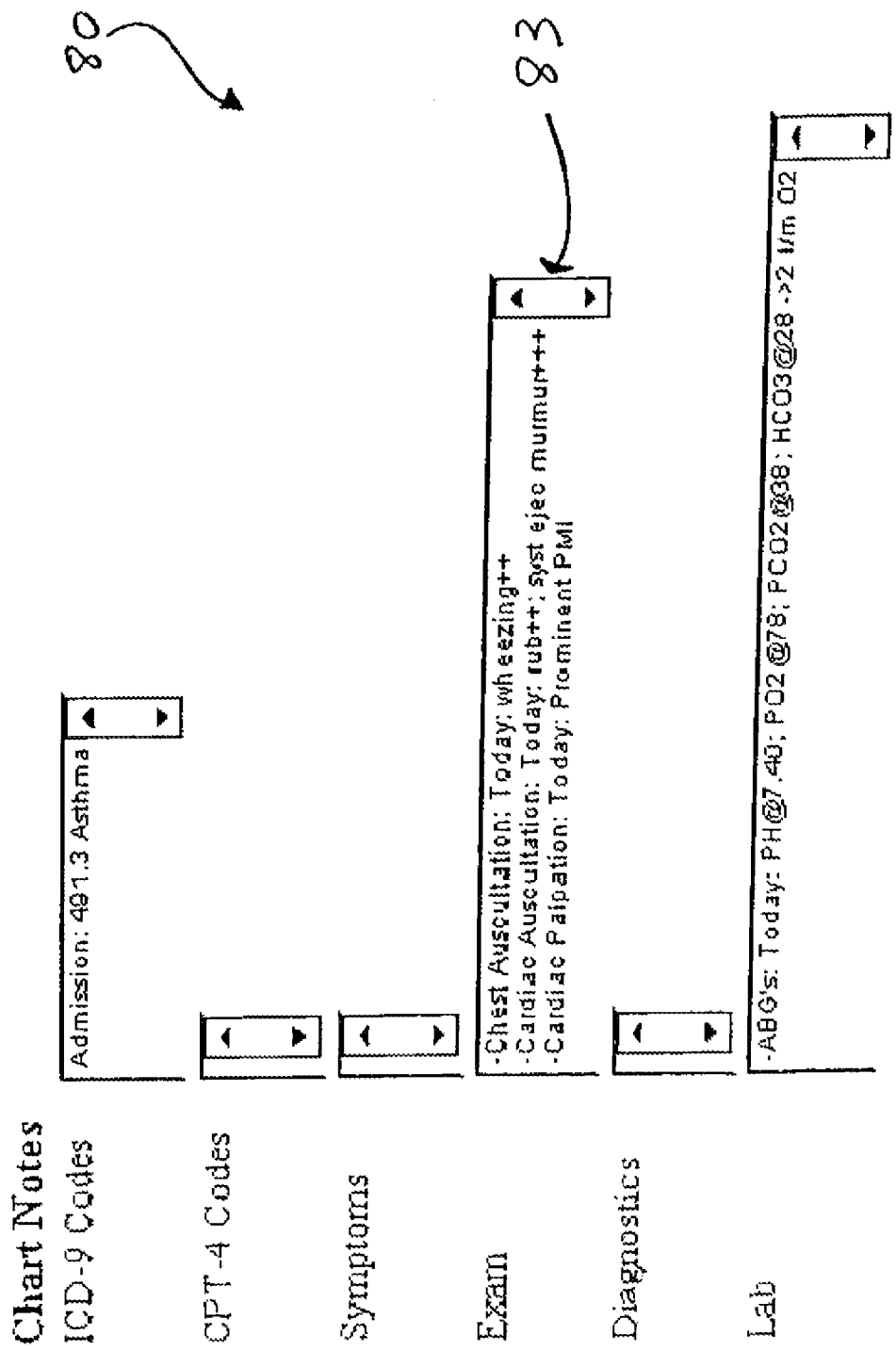
FIG. 4B illustrates a chart section of the Clinical screen of FIG. 4A.

FIG. 4B illustrates the Procedure Authorization screen display comprising an Procedures and a Clinical section.

The Procedures section enables manual entry of a CPT4 diagnosis code and diagnosis, or; manually entry can be done by entering as few as three letters to populate an adjacent pop-up button list which displays matching items for selection and entry, or an entry can be made by selection from the Procedure pop-up button list.

A computer implemented system for evaluating Emergency Room (ER) visits and clinical care for health care review organizations.

A computer implemented system comprising one or more computers, preferably at least two computers connected by the internet or a local area network comprising an Emergency Room system for evaluating Emergency Room (ER) visits and creating ER clinical charts for ER clinical care evaluation for health care review organizations, which: evaluates appropriateness of a patient visit by using the "Prudent Layperson Rule", and; creates an electronic clinical chart of relevant clinical data generated by one or more reasons for a patient ER visit and/or one or more diagnoses for the patient ER visit; and evaluates appropriateness of medical care for ER visit.

The Emergency Room system comprises: an Emergency Room Census screen, and; an Emergency Room Face Sheet screen, and; an Emergency Room Clinical screen display.

An Emergency Room Census screen displays the patients who have been registered, usually within the past 24 hours, and displays for each patient: the Date and Time of registration, and; an authorization number if the visit has been authorized, and; the discharge status of the patient describing discharge to home, admission as an inpatient, or discharge to another facility, and; the patient's presenting diagnosis or ICD9 code.

The Emergency Room Face screen enables the registration of an Emergency Room patient, and enables entry of: patient demographic data, and; entry of one or more symptoms or diagnoses.

An Emergency Room Face screen enables concurrent, real-time automated evaluation of patient symptoms, as well as diagnoses, to authorize an ER visit on basis of the "Prudent Lay Person Rule", wherein: An ER visit for one or more symptoms meeting "Prudent Lay Person Rule" is automatically authorized, without requiring input of clinical findings in a clinical chart. The single exception to this automatic authorization is if there is a "coordination of benefits" (COB) issue, where another party is financially responsible for the presenting symptom (eg. Chest pain always meets "Prudent Lay Person Rule"). If a symptom or symptoms can never meet the "Prudent Lay Person Rule", notification is given to the user (e.g. Earache never meets "Prudent Lay Person Rule").

FIG. 5A illustrates the Emergency Room Face screen authorizing the Emergency Room visit for chest pain, in the upper section, where the clickable "Auth Status" field displays text stating "Authorize ER visit. MEETS Prudent Layperson Rule". Clicking the "Go" submit button returns the user to the ER Census screen.

The lower section illustrates the portion of FIG. 5A illustrate the interactive pop-up button lists which consist of: A pop-up button list enabling the selection of a Symptom or an ICD9 code and illness, which: populates the Sx (Symptom)/Code Groups pop-up button list, which; populates the Symptoms/Codes pop-up button list, which; enters the symptom or the ICD9 code and illness into the Emergency Room Face screen.

FIG. 5B illustrates the Emergency Room Face screen for a patient presenting with the diagnosis of wrist fracture, where the clickable Auth Status field displays text stating "Go to CLINICAL screen. Requires additional data". The pop-up button list next to the "Go" submit button displays "Clinical screen" and clicking go brings up the Emergency Room Clinical screen display to enable creation of a clinical chart for the ER visit.

FIG. 5C illustrates ability to manually enter a few letters in the "Symptom/Dx" (Symptom/Diagnosis) field to populate an adjacent pop-up button list with symptoms and codes that include the manually entered letters, thereby: allowing the selection of a symptom or code for entry into the Emergency Room Face screen, and; setting the interactive pop-up button lists to the selected symptom or ICD9 code and diagnosis, and; symptoms which have an associated ICD9 code are displayed along with their ICD9 code.

Entered symptoms and diagnoses which have no "Prudent Layperson Rule" criteria or diagnosis based criteria require input of clinical findings and the user is then directed to the ER Clinical screen.

FIG. 5D illustrates an entry of a symptom without criteria. The Auth Status field displays the text stating "PENDED for review. No Criteria available. Enter clinical data."

The ER Clinical screen functions similarly to the Clinical screens of the Care Utilization Management System, wherein: In the ER Clinical screen, the criteria prompts are generated by selecting a presenting symptom (symptom causing the ER visit) or a diagnosis for the ER visit. As in the Clinical Screen of the Care Utilization Management System, an electronic clinical chart is created by the two-step "Prompt and Response Action" and authorization for the ER encounter is given when entered findings meet criteria.

If a patient is admitted to the hospital from the Emergency Room, the patient's clinical findings entered in the ER Clinical screen are also displayed when the Admission Clinical screen is initially displayed, thereby saving the user the need to repeat entry of these clinical findings.

In one embodiment, admission to the hospital for a patient in the emergency room requires pre-authorization for admission by the Emergency Room module. If authorization is not conferred, an on-duty medical director must be immediately contacted for preauthorization. If a medical director is not contacted, the admission is then presented for concurrent reviewed after admission.

A computer implemented Appeals system for health care providers for appeal of health care services denied by managed care organizations.

A computer implemented system comprising a plurality of computers connected by the internet or a local area network for an Appeals system, wherein the system is used by providers of health care services, and; enables the creation of an Appeal to a managed care organization for a denial of medical services, based on: clinical findings already entered in electronic charts, and; clinical findings entered electronically in rebuttal to reasons for denial of services, comprising a: Denials Registration screen display, and an Appeals Writer screen display.

The Denials Registration screen display enables the entry of a denial of payment of services by: Entering Patient identifying data, and by: entering the company denying payment, and by; entering a denied services, and by then; entering the denial reasons for the service, which then; displays the CPT4 code, procedure name and denial reason in the adjacent scrollable area.

The Rebuttals scrollable area displays clinical reasons for rebutting each denial and is populated by entries made in the Appeals Writer screen display after the user returns to the Denials Registration screen.

The Appeals Writer screen display enables the entry of clinical rebuttal entries for each denial of service. Appeals Writer screen display comprises: a Rebuttals section, and; a Clinical section.

The Rebuttals section displays each denied service and the reason for the denial in a scrollable area, as entered in the Denials Registration screen display. This may then display the clinical chart for the date of the denied service, if one exists, and; displays a rebuttal reason based on one or more findings in the clinical chart. This rebuttal is displayed in the Rebuttals scrollable area and comprises 2 lines. The first line displays the denied service and the reason for the denial. The second line (indented) displays the rebuttal statement. The Rebuttals scrollable area can display multiple paired lines of denied services and rebuttals. If there findings are not found in the clinical chart to rebut the denied service, the user is directed to the Clinical Review section, where; the Prompt pop-up list is populated with Parameters the clickable Navigator field text displays text describing the Prompts which enables automatic selection of prompts.

Selection of a Prompt guide the user for entry of clinical findings for the denied service, or; findings may be selected by user selection of Element, System/Group, Parameter and Finding pop-up button lists, or; the user may manually enter a finding.

The user may review the clinical charts for multiple dates, which; may change the Prompts pop-up button list, and; may change the Navigator field text display, and; enables entries of clinical findings for the rebuttal, and; a rebuttal reason may be manually entered in the field adjacent to the Rebuttals label, and user entry requires no scrolling of screen for user interaction.

The entries in the Rebuttals scrollable area are also displayed when the user returns to the Denials Registration screen display.

FIG. 6A illustrates the Denials Registration screen display.

FIG. 6B illustrates the Appeals Writer screen display.

A computer implemented system comprising one or more computers, preferably at least two computers connected by the internet or a local area network for creating electronic clinical charts.

A computer implemented system comprising one or more computers, preferably at least two computers connected by the internet or a local area network the creation of electronic clinical charts, based on the Clinical Care Utilization Management System, where;

The criteria prompts are populated by one or more diagnoses, or reasons, for the patient encounter, where; the two-step "Prompt and Response Action" enables rapid completion of an electronic clinical chart, where the clinical chart can be downloaded in Excel™ spreadsheet format to the clinician's user's own computer network for additional storage display and incorporation into the user's proprietary medical application.

In one embodiment, a clinician advisory area on the Clinical screen suggests further medical care such as treatment and diagnostic testing, based on the entered clinical findings. This advisory module has been downloaded with the user screen display to allow real-time, offered concurrently updated advice as each finding is entered.

In another embodiment, a clinician advisor area on the Clinical screen suggests a differential diagnosis for the patient encounter based on the patient's demographics and entered clinical findings. This differential diagnosis module has been downloaded with the user screen display to allow real-time, offered concurrently updated differential diagnoses as each finding is entered.

In one embodiment, the use of this module is supported by advertisements and/or by underwriting by third party organizations.

A computer implemented system comprising one or more computers, preferably at least two computers connected by the internet or a local area network enabling a patient to review the medical care provided by a clinician.

A computer implemented system comprising one or more computers, preferably at least two computers connected by the internet or a local area network enabling a layperson user to review a clinician's medical care referenced to a patient's specific medical status, and comprises:

Layperson Second Opinion system, comprising: a Patient 2nd Opinioner Face screen display, and; a Patient 2nd Opinioner Discussion Page screen display. The Patient Second Opinion Face screen display comprises the: Your illness section, where; aspects of an illness by a layperson which can be entered by; selection from pop-up button lists, or; manually entry by entering as few as three letters to populate an adjacent pop-up button list which displays matching items for selection and entry, and; Your Doctor's Care section, where; aspects of the doctor's care such as diagnoses, diagnostic tests, medications and/or need for hospitalization can be entered by: selection from the pop-up button lists, or; manually by entering as few as three letters to populate an adjacent pop-up button list which displays matching items for selection and entry.

Patient 2nd Opinioner Discussion screen display comprises a: Your Medical Issues section, and a; Q&A section, and a; Discussion section, and a; Referrals section.

The Your Medical Issues section displays the Your Illness and Your Doctor's Care scroll areas which had been entered in the Patient Second Opinion Face screen display, and; the Q &A section displays prompts, in the form of questions, to guide additional input of the patient's medical status by a layperson user, and where; there is a Question Navigator clickable text field to allow automatic selection of the questions, and where; the user can enter answers, in the form of clinical findings, by selection in pop-up lists or by manual entry, and where; the Discussion section displays a text scrollable area where there is an academic discussion of medical management of a patient such as described with the entered information about the illness, as well as an academic discussion of the care such as described in Doctor's Care, where; a discussion module has been downloaded with the user screen display to allow real-time, concurrently updated discussion as each question is answered, where; user entry requires no scrolling of screen for user interaction.

In the Referrals section, a user may select a medical specialty and enter a zip code, in order to display a scrollable list of doctors in the specialty in the user's area, where; in one embodiment, this list comprises doctors whose clinical care has been deemed appropriate by their earlier interactions with UMsource, or; in another embodiment, this list comprises doctor's who have contracted to be displayed in this list, or; in another embodiment, this list comprises doctors whose clinical care has been deemed appropriate by their earlier interactions with UMsource and who have contracted to be displayed in this list, and; in one embodiment of the Layperson Second Opinion Discussion system the use of this system is by payment of a user fee, or; in another embodiment, the use of this module is supported by advertisements and/or by underwriting by third party organizations.

FIG. 7A illustrates the Patient 2nd Opinioner Face screen display

Figure 7B:
FIG. 7B illustrates an example of the Clinical screen after clicking Navigator field.
Figure 8:
FIG. 8 illustrates an example of downloaded clinical notes in Excel™ spreadsheet format.
Figure 14:
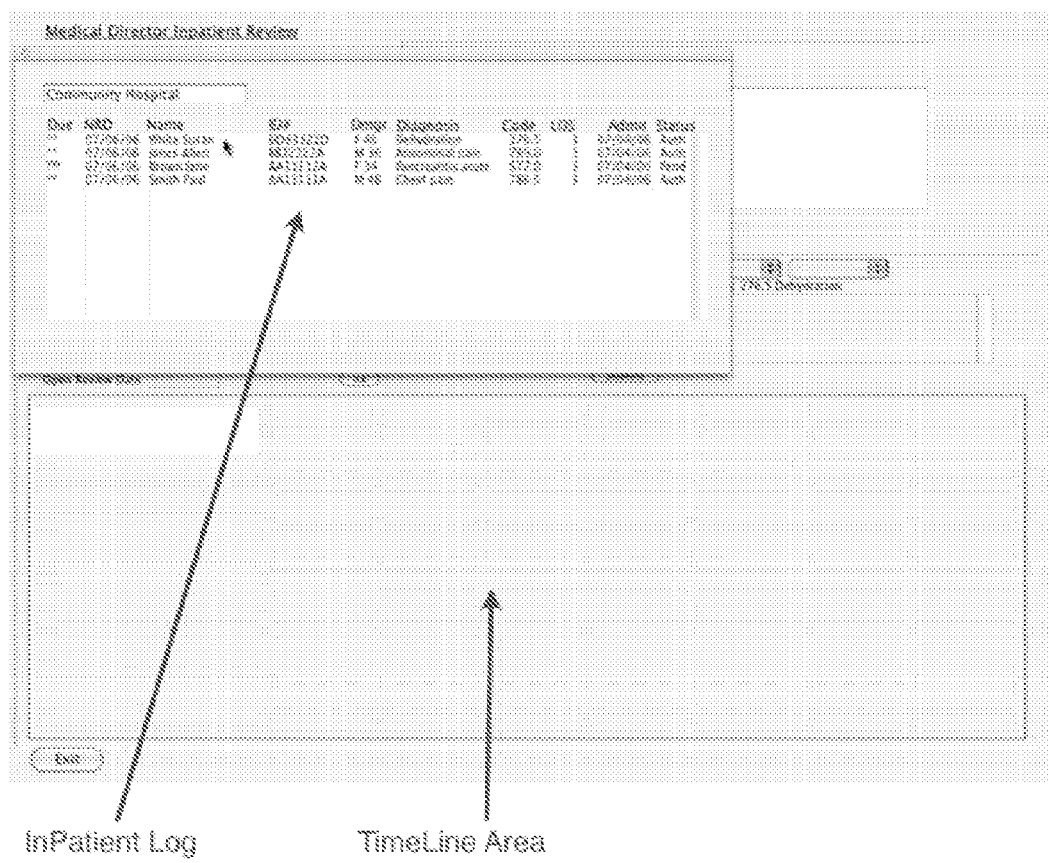
FIG. 14 is a screen capture illustrating an exemplary medical director inpatient review user interface, including an inpatient log.
Figure 15:
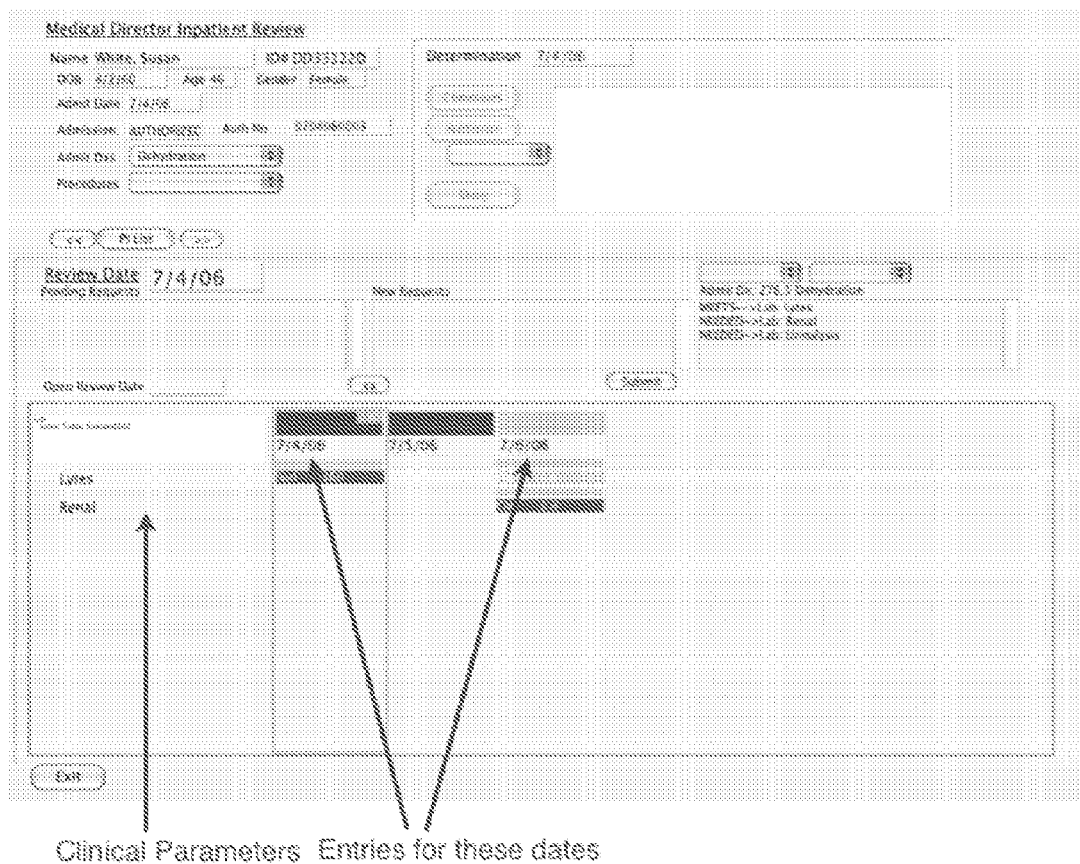
FIG. 15 is a screen capture illustrating an exemplary medical director inpatient review user interface comprising a timeline area, wherein entries have been entered in the timeline.
Figure 16:
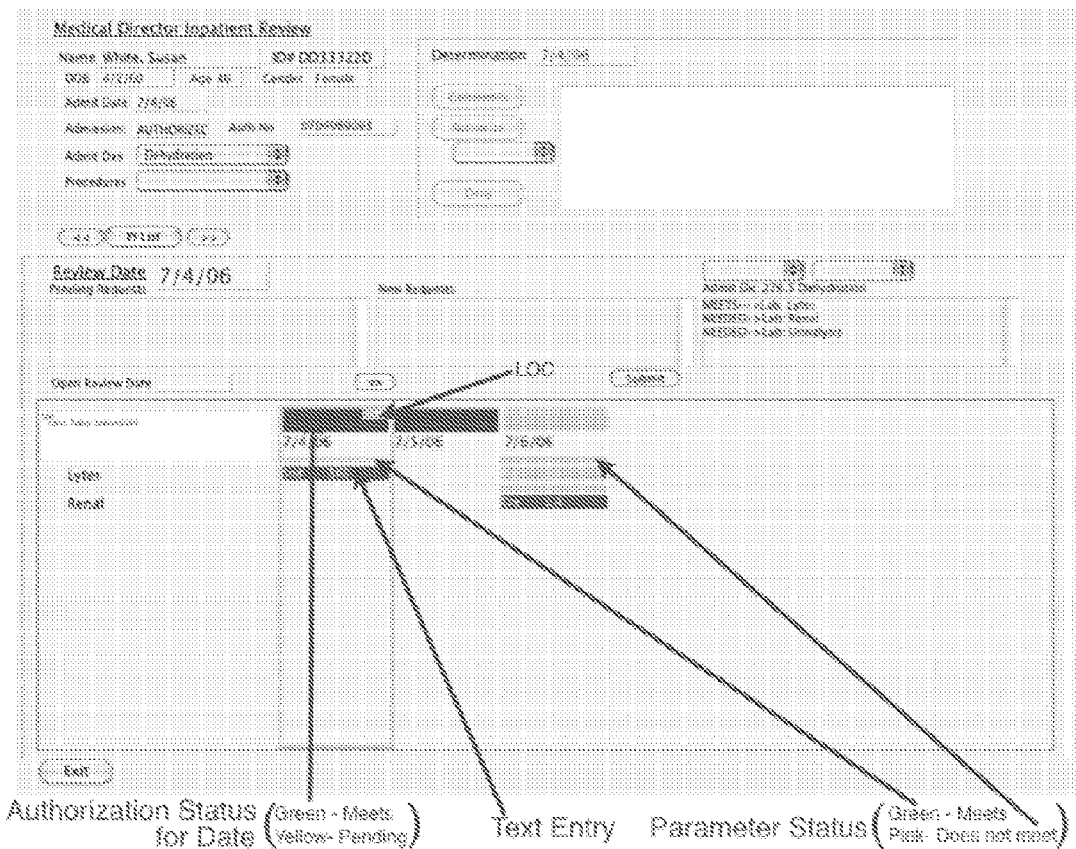
FIG. 16 is a screen capture illustrating an exemplary medical director inpatient review user interface, wherein color coding has been used to facilitate easy identification of the authorization status of various clinical data entries.
Figure 17:
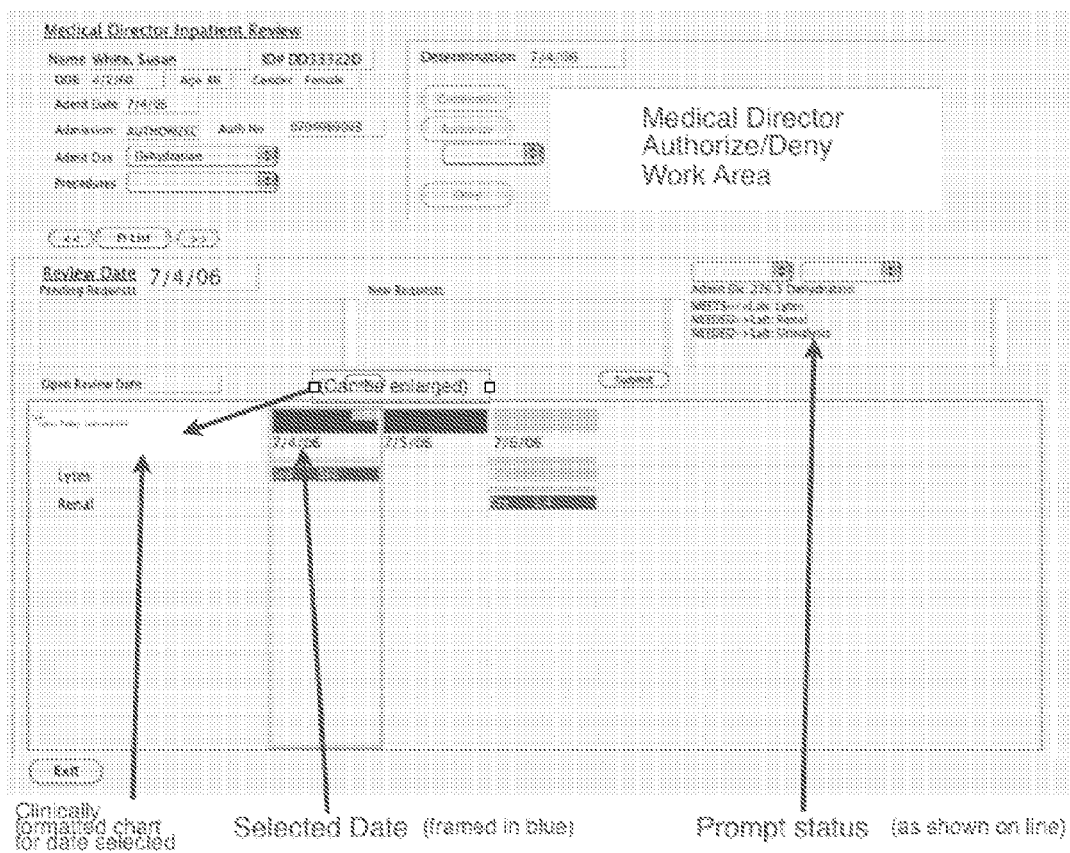
FIG. 17 is a screen capture illustrating an exemplary medical director inpatient review user interface, wherein additional details for a selected date are shown.
Figure 18:
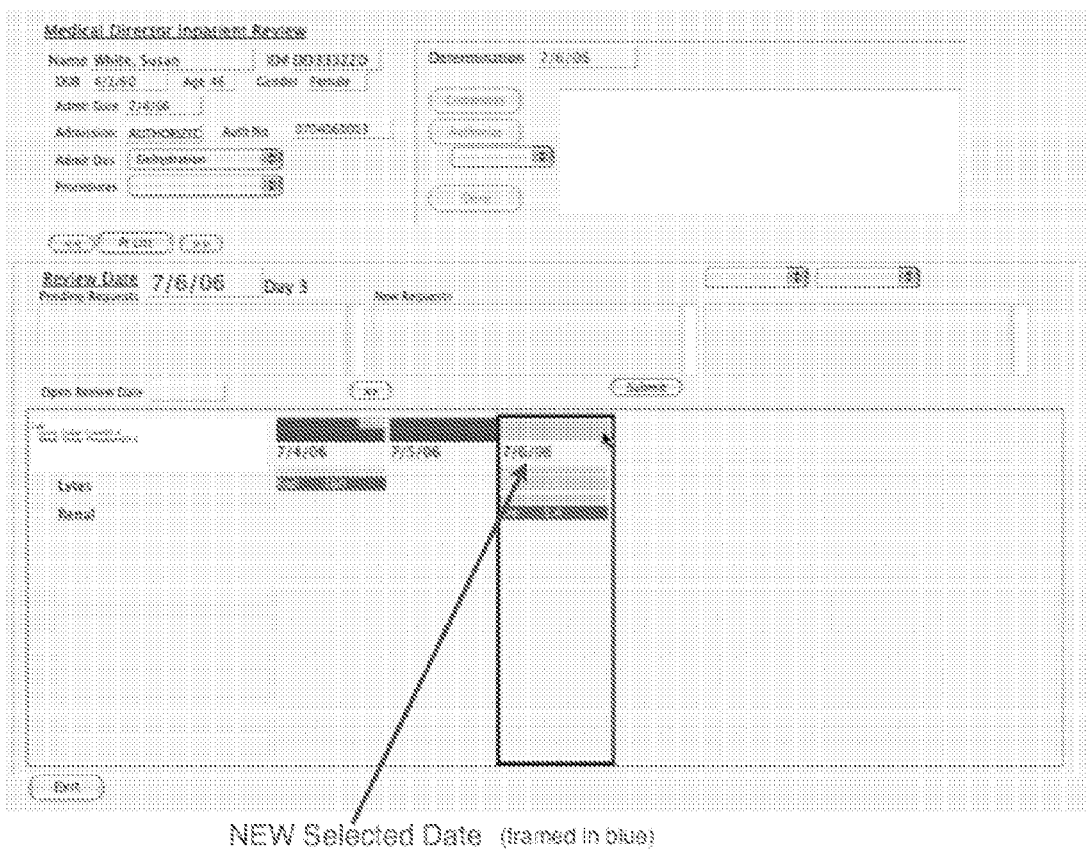
FIG. 18 is a screen capture illustrating an exemplary medical director inpatient review user interface, wherein a new date has been selected.
Figure 19:
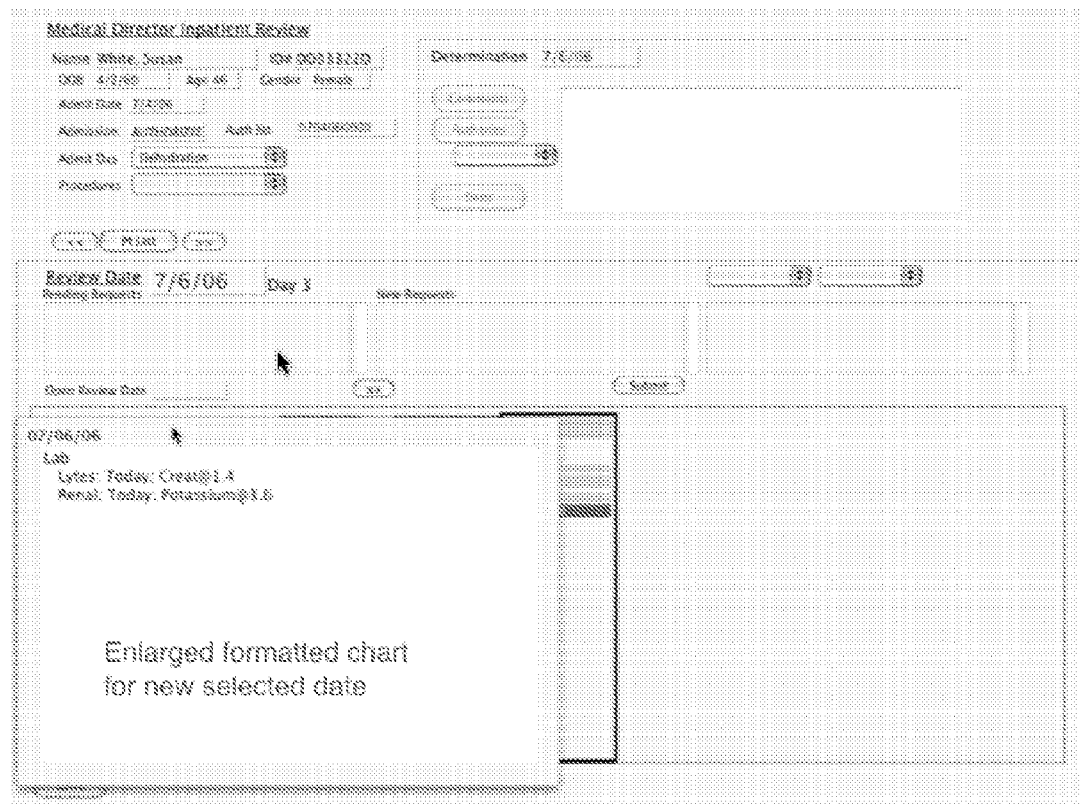
FIG. 19 is a screen capture illustrating an exemplary medical director inpatient review user interface

FIG. 7B illustrates the Patient 2nd Opinioner Discussion Page screen

Although the instant disclosure was discussed in terms of certain preferred embodiments, the description is not limited to such embodiments. Rather, the invention includes other embodiments including those apparent to a person of ordinary skill in the art. Thus, the scope of the invention should not be limited by the preceding description but should be ascertained by reference to the claims that follow.

What is claimed is:

1. A computer implemented system, consisting of one or more computers connected by one of an internet and a local area network, for generating an electronic clinical record, in clinical chart note format, of a patient clinical encounter for submission for review by a health care reviewing organization, comprising:

at least one selection interface module, the selection interface module adapted to facilitate the selection of at least a diagnosis; and a verification module for determining an authorization level for the diagnosis by referring to at least data in identified fields, the verification module determining said authorization level prior to submission of the clinical record via a web browser on the client side to a server computer, said selection interface module facilitating selection of criteria prompts in a prompt pop-up button list by display of a clickable navigator text field, text in the navigator field describes a set of criteria prompts which are selected to meet criteria for a diagnosis for a patient encounter;

wherein the criteria pop-up button list displays criteria based on a diagnosis or reason for the clinical encounter;

wherein a plurality of hierarchical pop up lists are automatically set in response to the selection of a criteria from the criteria pop-up button list;

the selection interface module presenting a criteria selection interface in a clinical format that is familiar to clinicians and healthcare reviewers, the criteria selection interface being presented to the user within a single screen while selecting criteria.

2. The system of claim 1, wherein said selection interface module facilitates one or more clinically formatted chart notes to be downloaded from the server computer in spreadsheet format to a user's computer system for on-screen display of multiple clinical charts in a single screen display.

3. The system of claim 1, wherein said selection interface module facilitates display of multiple clinical encounters by displaying a timeline with color codes and text, and each line of the timeline displays one of a parameter and a finding across multiple clinical encounters, with a single column forming a cell with the row representing one or more findings for each date of said patient encounter.

4. A computer implemented system, consisting of one or more computers connected by one of an internet and a local area network, for generating an electronic clinical record, in clinical chart note format, of a patient clinical encounter for submission for review by a health care reviewing organization, comprising:

at least one selection interface module, the selection interface module adapted to facilitate the selection of at least one reason for the patient clinical encounter; and a verification module for determining an authorization level for the at least one reason for the encounter by referring to at least data in identified fields, the verification module determining said authorization level prior to submission of the clinical record via a web browser on the client side to a server computer, said selection interface module facilitating selection of criteria prompts in a prompt pop-up button list by display of a clickable navigator text field, text in the navigator field describes a set of criteria prompts which are selected to meet criteria for the at least one reason for the patient clinical encounter;

wherein the criteria pop-up button list displays criteria based on a diagnosis or reason for the clinical encounter;

wherein a plurality of hierarchical pop up lists are automatically set in response to the selection of a criteria from the criteria pop-up button list;

the selection interface module presenting a criteria selection interface in a clinical format that is familiar to clinicians and healthcare reviewers, the criteria selection interface being presented to the user within a single screen while selecting criteria.

5. The computer implemented system according to claim 4, wherein the hierarchical pop-up lists comprise an element pop-up list, a system-group pop-up list, a parameter pop-up list and a finding pop-up list.

* * * * *